United States Patent
Clough et al.

(10) Patent No.: US 6,777,412 B2
(45) Date of Patent: *Aug. 17, 2004

(54) FUNGICIDES

(75) Inventors: John Martin Clough, Marlow (GB); Christopher Richard Ayles Godfrey, Bracknell (GB); Ian Thomas Streeting, Wokingham (GB); Rex Cheetham, Bracknell (GB); Paul John de Fraine, Wokingham (GB); David Bartholomew, Wokingham (GB); James John Eshelby, Camberley (GB)

(73) Assignee: Syngenta Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/608,698

(22) Filed: Jun. 27, 2003

(65) Prior Publication Data

US 2004/0092746 A1 May 13, 2004

Related U.S. Application Data

(62) Division of application No. 10/087,984, filed on Mar. 5, 2002, now Pat. No. 6,613,773, which is a continuation of application No. 08/486,060, filed on Jun. 7, 1995, now abandoned, which is a continuation of application No. 08/146,822, filed on Nov. 1, 1993, now abandoned, which is a continuation of application No. 07/736,159, filed on Jul. 26, 1991, now abandoned.

(30) Foreign Application Priority Data

Jul. 27, 1990 (GB) ................................................ 9016583
Sep. 24, 1990 (GB) ................................................ 9020748

(51) Int. Cl.$^7$ .......................... A01N 43/54; C07D 239/52
(52) U.S. Cl. ............. 514/247; 514/252.01; 514/252.02; 514/252.03; 514/252.04; 514/252.05; 544/182; 544/239; 544/240; 544/238
(58) Field of Search .......................... 514/247, 252.01, 514/252.02, 252.03, 252.04, 252.05; 544/182, 239, 240, 238

(56) References Cited

U.S. PATENT DOCUMENTS

| | | |
|---|---|---|
| 5,008,276 A | 4/1991 | Clough et al. |
| 5,057,146 A | 10/1991 | Anthony et al. |
| 5,059,605 A | 10/1991 | Clough et al. |
| 5,145,856 A | 9/1992 | Clough et al. |
| 5,194,438 A | 3/1993 | Schuetz et al. |
| 5,229,391 A | 7/1993 | Clough et al. |
| 5,264,440 A | 11/1993 | Clough et al. |
| 5,314,892 A | 5/1994 | Clough et al. |
| 5,633,256 A | 5/1997 | Anthony et al. |
| 6,613,773 B2 * | 9/2003 | Clough et al. ............ 514/269 |

FOREIGN PATENT DOCUMENTS

| | | |
|---|---|---|
| EP | 242081 | 10/1987 |
| EP | 307103 | 3/1989 |
| EP | 382375 | 8/1990 |
| EP | 393861 | 10/1990 |
| EP | 430471 | 6/1991 |

OTHER PUBLICATIONS

M. Elliott et al., "Synthetic Pyrethroids—A New Class of Insecticide", Chem. Soc. Reviews. 1979, vol. 7, pp. 473–505.

Coghlin et al., "Novel Agents for the Control of Cereal and Grape Powdery Mildew", A.C.S. Symposium Series 443, Synthesis and Chemistry of Agrochemicals II, American Chemical Society, Washington, D.C. (1991).

Abstracts of Papers, 198$^{th}$ ACS National Meeting, American Chemical Society, Miami Beach, FL, Sep. 10–15, 1989, Abstract No. 73.

* cited by examiner

*Primary Examiner*—Zinna Northington Davis
(74) *Attorney, Agent, or Firm*—Rose M. Allen

(57) ABSTRACT

The invention provides fungicidal compounds of formula (I) or stereoisomers thereof:

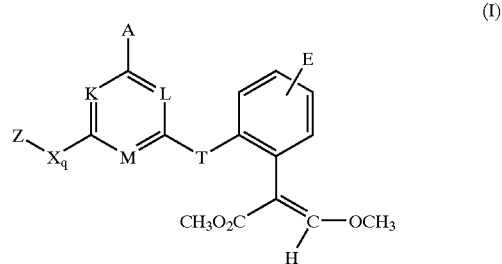

(I)

wherein X is $CH_2O$; A is hydrogen; E is hydrogen; q is 1; any two of K, L and M are nitrogen and the other is CH; T is oxygen or sulfur; and Z is an optionally substituted phenyl group or an optionally substituted heterocylyl group.

26 Claims, No Drawings

FUNGICIDES

This application is a divisional application of U.S. application Ser. No. 10/087,984 filed Mar. 5, 2002, now U.S. Pat. No. 6,613,773, which is a continuation of U.S. application Ser. No. 08/486,060 filed Jun. 7, 1995, now abandoned, which is a continuation of U.S. application Ser. No. 08/146,822 filed Nov. 1, 1993, now abandoned, which a continuation of U.S. application Ser. No. 07/736,159 filed Jul. 26, 1991, now abandoned.

This invention relates to derivatives of propenoic acid useful as fungicides, to processes for preparing them, to fungicidal compositions containing them, and to methods of using them to combat fungi, especially fungal infections of plants.

A range of pesticidal alkyl 2-(substituted)pyridinyl- and pyrimidinyloxyphenyl-3-alkoxypropenoates is described in EP-A-0242081.

The present invention provides a compound having the formula (I), and stereoisomers thereof, in which any two of K, L and H are nitrogen and the other is CB; T is oxygen or sulphur; Z is optionally substituted aryl or optionally substituted heterocyclyl; X is O, $S(O)_n$, $NR^4$, $N(CHO)$, $CR^1R^2$, $CHR^5$, CO, $CR^1(OR^2)$, $C=CR^1R^2$, $CHR^1CHR^2$, $CR^1=CR^2$, $CHR^1CR^2=CH$, $C\equiv C$, $OCHR^1$, $CHR^1O$, $CH(CF_3)O$, $CH(CN)O$, $OCHR^1O$, $S(O)_nCHR^1$, $S(O)_nCHR^1O$, $CHR^1S(O)_n$, $CHR^1OSO_2$, $NR^4CHR^1$, $CHR^1NR^4$, $CO_2$, $O_2C$, $SO_2O$, $OSO_2$, $CO.CO$, $COCHR^1$, $COCHR^1O$, $CHR^1CO$, $CHOH.CHR^1$, $CHR^1.CHOH$, $\Psi$, Q (for the meaning of $\Psi$ and Q, see under "Chemical Formulae" later), $CONR^4$, $OCONR^4$, $NR^4CO$, $CSNR^4$, $OCS.NR^4$, $SCO.NR^4$, $NR^4CO_2$, $NR^4CS$, $NR^4CSO$, $NR^4COS$, $NR^4CONR^4$, $S(O)_nNR^4$, $NR^4S(O)_n$, $CS_2$, $S_2C$, $CO.S$, $SCO$, $N=N$, $N=CR^1$, $CR^1=N$, $CHR^1CHR^2CH(OH)$, $CHR^1OCO$, $CHR^1SCO$, $CHR^1NR^4CO$, $CHR^1NR^4CONR^4$, $CHR^1CHR^2CO$, $CR^1NO$, $C(NR^1R^2)=NO$, $ON=CR^1$, $ON=C(NR^1R^2)$, $CHR^1ON=CR^2$, $CO.OCR^1R^2$, $CHR^1CHR^2CHR^3$, $OCHR^1CHR^2$, $(CH_2)_mO$, $CHR^1OCHR^2$, $CHR^1CHR^2O$, $OCHR^1CHR^2O$, $S(O)_nCHR^1CHR^2$, $SCHR^1CHR^2O$, $CHR^1S(O)_nCHR^2$, $CHR^1CHR^2S(O)_n$, $CR^1=NNR^4$, $NR^4N=CR^1$, $CHR^1CONR^2$, $CHR^1OCO.NR^2$, $CH=CHCH_2O$, $C\equiv CCH_2O$, $COCHR^1CHR^2O$, or $(R^5)_2P^+CHR^2O^-$; A, B and E, which may be the same or different, are H, hydroxy, halo, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R^1$, $R^2$ and $R^3$, which may be the same or different, are H, $C_{1-4}$ alkyl or phenyl; $R^4$ is H, $C_{1-4}$ alkyl or $COR^1$; $R^5$ is optionally substituted phenyl; $O^-$ is a halide anion; n is 0, 1 or 2, m is 3, 4 or 5, and q is 0 or 1; provided that when q is 0 and Z is an optionally substituted 3- to 6-membered heterocyclic ring containing at least one trivalent nitrogen atom, Z is not attached to the central pyrimidine ring by said trivalent nitrogen atom, and that when q is 1 and X is 0, Z is not optionally substituted phenyl or optionally substituted pyridinyl.

Because the double bond of the propenoate group is unsymmetrically substituted, the compounds of the invention may be obtained in the form of mixtures of (E)- and (Z)-geometric isomers. However, these mixtures can be separated into individual isomers, and this invention embraces such isomers and mixtures thereof in all proportions including those which consist substantially of the (Z)-isomer and those which consist substantially of the (E)-isomer. The (E)-isomer, in which the groups —$CO_2CH_3$ and —$OCH_3$ are on opposite sides of the olefinic bond of the propenoate group, are the more fungicidally active and form a preferred embodiment of the invention.

The substituent Z in compound (I) is optionally substituted aryl or optionally substituted heterocyclyl. Where valency allows, each of the optionally substituted groups aryl or heterocyclyl can carry up to 5 substitutents. The term "aryl" includes phenyl in particular, and naphthyl. The term "heterocyclyl" includes 5- and 6-membered heterocyclic groups containing one or more of each of the heteroatoms O, S and N (preferably S or N), fused benzenoid and heteroaromatic ring systems, and, in each case, the corresponding N-oxides. Examples of heterocyclyl groups which Z may be, except where otherwise indicated, are pyridinyl, pyrimidinyl, pyrazinyl, pyridazinyl, 1,2,3-, 1,2,4-, and 1,3,5-triazinyl, 1,2,4,5-tetrazinyl, 1,2,3- and 1,2,4-triazolyl, imidazolyl, thienyl, furyl, pyrrolyl, pyrazolyl, thiazolyl, isothiazolyl, oxazolyl, isoxazolyl, 1,2,4- and 1,3,5-thiadiazolyl, oxadiazolyl, purinyl, quinolinyl, isoquinolinyl, quinoxalinyl, benzothienyl, benzoxazolyl, benzthiazolyl, piperidinyl, morpholinyl, pyrrolidinyl and tetrahydrofuranyl, and, where appropriate, the corresponding N-oxides. Substituents which may be present in the optionally substituted aryl and heterocyclyl moieties include one or more of the following; halo, hydroxy, oxo, mercapto, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo($C_{1-4}$)alkyl (especially trifluoromethyl), halo($C_{1-4}$)alkoxy (especially trifluoromethoxy), $C_{1-4}$ alkylthio (especially methylthio), $C_{2-4}$ alkenylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$) alkyl, optionally substituted aryl (especially optionally substituted phenyl), optionally substituted heterocyclyl (especially optionally substituted pyridinyl or pyrimidinyl), optionally substituted aryloxy (especially optionally substituted phenoxy), optionally substituted phenylthio, optionally substituted heteroaryloxy (especially optionally substituted pyridinyloxy or pyrimidinyloxy), optionally substituted aryl ($C_{1-4}$)alkyl (especially optionally substituted benzyl, optionally substituted phenethyl and optionally substituted phenyl-n-propyl) in which the alkyl moiety is optionally substituted with hydroxy, optionally substituted heteroaryl($C_{1-4}$)alkyl (especially optionally substituted pyridinyl-or pyrimidinyl ($C_{1-4}$)alkyl), optionally substituted aryl($C_{2-4}$)alkenyl (especially optionally substituted phenylethenyl), optionally substituted heteroaryl($C_{2-4}$)alkenyl (especially optionally substituted pyridinylethenyl, pyrimidinylethenyl or 1-(imidazol-1-yl)vinyl), optionally substituted aryl($C_{1-4}$) alkoxy (especially optionally substituted benzyloxy), optionally substituted heteroaryl($C_{1-4}$)alkoxy (especially optionally substituted pyridinyl- or pyrimidinyl($C_{1-4}$)alkoxy), optionally substituted aryloxy($C_{1-4}$)alkyl (especially phenoxymethyl), optionally substituted heteroaryloxy($C_{1-4}$) alkyl (especially optionally substituted pyridinyloxy- or pyrimidinyloxy($C_{1-4}$)-alkyl), acyloxy, including $C_{1-4}$ alkanoyloxy (especially acetyloxy) and benzoyloxy, cyano, isocyano, thiocyanato, isothiocyanato, nitro, —NR'R", —$N_3$, —NHCONR'R", —NR'COR", —CONR'R", CR'=NOR", CHR'CO$_2$R", CSNR'R", —CO$_2$R', —OSO$_2$R', —SO$_2$R', —SOR', SO$_2$OR', SO$_2$NR'R", —COR', —OCOR', —CR'=NR", N=CHNR'R", NHSO$_2$R' or —N=CR'R" in which R' and R" are independently hydrogen, hydroxy, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, $C_{2-4}$ alkenyl, $C_{2-4}$ alkenyloxy, phenyl, phenoxy or benzyl, the phenyl, phenoxy and benzyl groups being optionally substituted with halogen, $C_{1-4}$ alkyl or $C_{1-4}$ alkoxy, or two substituents when ortho to one another join to form a 5- or 6-membered aliphatic or aromatic ring optionally containing one or more oxygen, sulphur or nitrogen atoms.

Substituents which may be present in the aryl or heterocyclyl rings of any of the foregoing substituents and in the phenyl ring of $R^5$ include one or more of the following; halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$) alkyl, halo($C_{1-4}$)alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, alkanoyloxy, benzyloxy, cyano, thiocyanato, nitro, —NR'R", —NHCOR', —NHCONR'R", —CONR'R", —$CO_2$R', —$OSO_2$R', —$SO_2$R', —COR', —CR'=NR" or —N=CR'R" in which R' and R" have the meanings given above. The aliphatic moieties of any of the substituents may themselves be substituted with one or more of halogen, cyano, OR', SR', NR'R", $SiR'_3$ or OCOR', in which R' and R" have the meanings given above.

When any of the substituents A, B and E are $C_{1-4}$ alkyl or $C_{1-4}$ alkoxy, the alkyl moiety can be in the form of straight or branched chains, that is, the moiety may be methyl, ethyl, n- or iso-propyl, or n-, sec-, iso- or t-butyl. Other references herein to $C_{1-4}$ alkyl and $C_{1-4}$ alkoxy carry the same meaning. Cycloalkyl groups contain from 3 to 6 carbon atoms and include cyclopropyl and cyclohexyl. $C_{2-4}$ Alkenyl groups can be in the form of straight or branched chains and, where appropriate, may have either the (E)- or (Z)-configuration. Examples of such groups are vinyl, allyl, —C($CH_3$)=$CH_2$, and (E)- and (Z)-crotyl.

Halogen is typically fluorine, chlorine or bromine.

The ring containing K, L and M in formula (I) is a pyrimidine ring which may be joined to T and $Z(X)_q$ by any two of its ring carbon atoms adjacent to a ring nitrogen atom. Of particular interest are those compounds of formula (I) in which K and L are both nitrogen and M is CB.

In one aspect, the invention provides a compound having the formula (I), and stereoisomers thereof, in which any two of K, L and M are nitrogen and the other is CB; T is oxygen or sulphur; Z is optionally substituted aryl or optionally substituted heteroaryl; X is $S(O)_n$, $NR^4$, N(CHO), $CR^1R^2$, $CHR^5$, CO, $CR^1(OR^2)$, C=$CR^1R^2$, $CHR^1CHR^2$, $CR^1$=$CR^2$, $CHR^1CR^2$=CH, C≡C, $OCHR^1$, $CHR^1$O, CH($CF_3$)O, CH(CN)O, $OCHR^1$O, $S(O)_nCHR^1$, $S(O)_n$ $CHR^1$O, $CHR^1S(O)_n$, $CHR^1OSO_2$, $NR^4CHR^1$, $CHR^1NR^4$, $CO_2$, $O_2$C, $SO_2$O, $OSO_2$, CO.CO, $COCHR^1$, $COCHR^1$O, $CHR^1$CO, CHOH.$CHR^1$, $CHR^1$.CHOH, Ψ, Q (for the meaning of Ψ and Q, see under "Chemical Formulae" later), $CONR^4$, $OCONR^4$, $NR^4$CO, $CSNR^4$, OCS.$NR^4$, SCO.$NR^4$, $NR^4CO_2$, $NR^4$CS, $NR^4$CSO, $NR^4$COS, $NR^4CONR^4$, $S(O)_n$ $NR^4$, $NR^4S(O)_n$, $CS_2$, $S_2$C, CO.S, SCO, N=N, N=$CR^1$, $CR^1$=N, $CHR^1CHR^2$CH(OH), $CHR^1$OCO, $CHR^1$SCO, $CHR^1NR^4$CO, $CHR^1CHR^2$CO, O.N=$CR^1$, $CHR^1$O.N=$CR^2$, CO.$OCR^1R^2$, $CHR^1CHR^2CHR^3$, $OCHR^1CHR^2$, $(CH_2)_m$O, $CHR^1OCHR^2$, $CHR^1CHR^2$O, $OCHR^1CHR^2$O, $S(O)_nCHR^1CHR^2$, $SCHR^1CHR^2$O, $CHR^1S(O)_nCHR^2$, $CHR^1CHR^2S(O)_n$, $CR^1$=$NNR^4$, $NR^4$N=$CR^1$, $CHR^1CONR^2$, $CHR^1$OCO.$NR^2$, CH=$CHCH_2$O, C≡$CCH_2$O, $COCHR^1CHR^2$O, or $(R^5)_2P^+$ $CHR^2Q^-$; A, B and e, which may be the same or different, are H, hydroxy, halo, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R^1$, $R^2$ and $R^3$, which may be the same or different, are H, $C_{1-4}$ alkyl or phenyl; $R^4$ is H, $C_{1-4}$ alkyl or $COR^1$; $R^5$ is optionally substituted phenyl; $Q^-$ is a halide anion; n is 0, 1 or 2, m is 3, 4 or 5, and q is 0 or 1; provided that when q is 0 and Z is an optionally substituted 3-to 6-membered heterocyclic ring containing at least one trivalent nitrogen atom, Z is not attached to the central pyrimidine ring by said trivalent nitrogen atom.

In this aspect of the invention, "aryl" includes phenyl in particular, and naphthyl, and "heteroaryl" includes 5- and 6-membered heterocyclic groups containing one or more of each of the heteroatoms O, S and N (preferably S or N), fused benzenoid and heteroaromatic ring systems, and, in each case, the corresponding N-oxides. Where valency allows, each of the optionally substituted groups aryl or heteroaryl can carry up to 5 substituents. Examples of heteroaryl groups which Z may be are pyridinyl, pyrimidinyl, pyrazinyl, pyridazinyl, 1,2,3-, 1,2,4-, and 1,3,5-triazinyl, 1,2,4,5-tetrazinyl, 1,2,3- and 1,2,4-triazolyl, thienyl, furyl, pyrrolyl, thiazolyl, purinyl, oxadiazolyl, quinolinyl, isoquinolinyl, quinoxalinyl, benzothienyl, benzoxazolyl and benzthiazolyl and, where appropriate, the corresponding N-oxides. Substituents which may be present in the optionally substituted aryl and heteroaryl moieties include one or more of the following; halo, hydroxy, oxo, mercapto, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo($C_{1-4}$)alkyl (especially trifluoromethyl), halo($C_{1-4}$)alkoxy (especially trifluoromethoxy), $C_{1-4}$ alkylthio (especially methylthio), hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$) alkyl, optionally substituted aryl (especially optionally substituted phenyl), optionally substituted heteroaryl (especially optionally substituted pyridinyl or pyrimidinyl), optionally subtituted aryloxy (especially optionally substituted phenoxy), optionally substituted heteroaryloxy (especially optionally substituted pyridinyloxy or pyrimidinyloxy), optionally substituted aryl($C_{1-4}$)alkyl (especially optionally substituted benzyl, optionally substituted phenethyl and optionally substituted phenyl-n-propyl) in which the alkyl moiety is optionally substituted with hydroxy, optionally substituted heteroaryl($C_{1-4}$)alkyl (especially optionally substituted pyridinyl- or pyrimidinyl ($C_{1-4}$)alkyl), optionally substituted aryl($C_{2-4}$)alkenyl (especially optionally substituted phenylethenyl), optionally substituted heteroaryl($C_{2-4}$)alkenyl (especially optionally substituted pyridinylethenyl or pyrimidinylethenyl), optionally substituted aryl($C_{1-4}$)alkoxy (especially optionally substitued benzyloxy), optionally substituted heteroaryl($C_{1-4}$) alkoxy (especially optionally substituted pyridinyl- or pyrimidinyl($C_{1-4}$)alkoxy), optionally substituted aryloxy ($C_{1-4}$)alkyl (especially phenoxymethyl), optionally substituted heteroaryloxy($C_{1-4}$)alkyl (especially optionally substituted pyridinyloxy- or pyrimidinyloxy($C_{1-4}$)alkyl), acyloxy, including $C_{1-4}$ alkanoyloxy (especially acetyloxy) and benzoyloxy, cyano, thiocyanato, nitro, —NR'R", —NHCOR', —NHCONR'R", —CONR'R", —$CO_2$R', —$OSO_2$R', —$SO_2$R', —COR', —CR'=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

Substituents which may be present in the aryl or heteroaryl rings of any of the foregoing substituents and in the phenyl ring of $R^5$ include one or more of the following; halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$) alkyl, halo($C_{1-4}$)alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, alkanoyloxy, benzyloxy, cyano, thiocyanato, nitro, —NR'R", —NHCOR', —NHCONR'R", —CONR'R", —$CO_2$R', —$OSO_2$R', —$SO_2$R', —COR', —CR'=NR" or —N=CR'R" in which R' and R" have the meanings given above.

In another aspect, the invention provides a compound having the formula (1.1), in which any two of K, L and M are nitrogen and the other is CB; X is $S(O)_n$ in which n is 0, 1 or 2, NH, $NCH_3$, $NCH_2CH_3$, $NCOCH_3$, $NCH(CH_3)_2$, $CH_2$, $CH(CH_3)$, $C(CH_3)_2$, CO, $C=CH_2$, $C=C(CH_3)_2$, $CH_2CH_2$, $CH(CH_3)CH_2$, $CH_2CH(CH_3)$, (E)-CH=CH, (Z)—CH=CH, (E)-$C(CH_3)$=$C(CH_3)$, C≡C, C≡$CCH_2O$, $OCH_2$, $OCH(CH_3)$, $(CH_2)_pO$ in which p is an integer of 1 to 5, $CH(CH_3)O$, CH(CN)O, $CH(CF_3)O$, $SCH_2$, $SCH(CH_3)$, $S(O)CH_2$, $S(O)CH(CH_3)$, $S(O)_2CH_2$, $S(O)_2CH(CH_3)$, $CH_2S$, $CH(CH_3)S$, $CH_2S(O)$, $CH(CH_3)S(O)$, $CH_2S(O)_2$, $CH(CH_3)S(O)_2$, $NHCH_2$, N(CHO), $N(CH_3)CH_2$, $N(COCH_3)CH_2$, $NHCH(CH_3)$, $N(CH_3)CH(CH_3)$, $N(COCH_3)CH(CH_3)$, $CH_2NH$, $CH_2N(CH_3)$, $CH_2N(COCH_3)$, $CH(CH_3)NH$, $CH(CH_3)N(CH_3)$, $CH(CH_3)N(COCH_3)$, $CO_2$, $O_2C$, $SO_2O$, $OSO_2$, CO.CO, $COCH_2$, $COCH(CH_3)$, $CON(COC_6H_5)$, $CH_2CO$, $CH(CH_3)CO$, $CH(OH)CH_2$, $CH(OH)CH(CH_3)$, $CH_2CH(OH)$, CH(OH) CH(OH), CONH, $CON(CH_3)$, $CON(CH_2CH_3)$, CON (CHO), $CON(COCH_3)$, NHCO, $N(CH_3)CO$, $N(CH_2CH_3)$ CO, N(CHO)CO, $N(COCH_3)CO$, $CSN(CH_3)$, CSNH, NHCS, $N(CH_3)CS$, $SO_2NH$, $SO_2N(CH_3)$, $NHSO_2$, $N(CH_3)$ $SO_2$, $N(CH_2CH_3)SO_2$, $CS_2$, $S_2C$, COS, SCO, (E)-N=N, (E)-N=CH, (E)-N=$C(CH_3)$, (E)-$CH_2$=N, (E)-$C(CH_3)$ =N, $CH_2CH_2CH_2$, $CH(CH_3)CH_2CH_2$, $CH_2CH(CH_3)CH_2$, $CH_2CH_2CH(CH_3)$, $OCH_2CH_2$, $CH_2OCH_2$, $SCH_2CH_2$, S(O) $CH_2CH_2$, $S(O)_2CH_2CH_2$, $SCH_2CH_2O$, $CH_2SCH_2$, $CH_2S(O)$ $CH_2$, $CH_2S(O)_2CH_2$, $CH_2CH_2S$, $CH_2CH_2S(O)$, $CH_2CH_2S$ $(O)_2$, (E)-CH=NNH, (E)-$C(CH_3)$=NNH, (E)-CH=NN $(CH_3)$, (E)-NHN=CH, (E)-NHN=$C(CH_3)$, (E)-$N(CH_3)$ N=CH, $CH_2CONH$, $CH(CH_3)CON(CH_3)$, $CH(CH_3)CON$ $(CH_3)$, (E)-CH=$CHCH_2O$, $COCH_2CH_2O$, Φ, θ (for the meaning of Φ and θ, see under "Chemical Formulae" later), $CH(C_6H_5)$, $COCH_2O$, CH(OH), $CO_2CH_2$, $(C_6H_5)_2P^+$ $CH_2Br^-$, $CH_2OCO$, $CH_2NHCO$, $CO_2SCO$, $OCH_2O$, $OCH_2CH_2O$, $S(O)CH_2O$, $COCH(CH_3)O$, (E)- $CH_2ON$=CH, (Z)-$CH_2ON$=CH, $CH_2CH_2CH(OH)$ (E)- $CH_2CH$=CH, $C(CH_3)(OH)$, $CH_2OSO_2$, $CH_2NHCO.NH$, OCO.NH, NHCO.NH or $CH_2OCO.NH$; q is 0 or 1; A and B are independently H, halo, $C_{1-4}$ alkyl, $C_{1-4}$ alkoxy, $C_{1-4}$ alkylthio or amino; E is H or halo; D is H, hydroxy, halo, $C_{1-4}$ alkyl, $C_{1-4}$ alkoxy, nitro, cyano, halo($C_{1-4}$)alkyl (especially trifluoromethyl), halo($C_{1-4}$)-alkoxy (especially trifluoromethoxy), phenyl, phenoxy, $NHCOR^6$ $NHSO_2R^6$, $NR^7R^8$, $CO_2R^7$, wherein $R^6$ is $C_{1-4}$ alkyl (especially methyl) or phenyl and $R^7$ and $R^8$ are independently H or $C_{1-4}$ alkyl, or $CH_3O_2C.C$=$CH.OCH_3$; and G is H, halo, $C_{1-4}$ alkyl, $C_{1-4}$ alkoxy or nitro; or D and G, when they are adjacent, join to form a benzene or pyridine ring.

More particularly, the invention includes a compound having the formula (I.1) in which any two of K, L and M are nitrogen and the other is CB; X is $S(O)_n$ in which n is 0, 1 or 2, $CH_2$, $CH_2CH_2$, $OCH_2$, $(CH_2)_pO$ in which p is an integer of 1 to 5, $OCH_2O$, $OCH_2CH_2O$, $SCH_2CH_2O$, CH(OH), CO, $CO_2$, $O_2C$, COS, SCO, $CO_2CH_2$, $SO_2O$, (Z)-CH=CH, (E)-CH=CH, (E)-CH=$CHCH_2O$, C≡$CCH_2O$, $CH(CH_3)O$, $SCH_2$, $SCH_2O$, $S(O)CH_2$, S(O) $CH_2O$, CH(CN)O, $CH(CF_3)O$, $S(O)_2CH_2$, CONH, CSNH, NH, $NCH_3$, $CH_2NH$, $N(CH_3)CH_2$, NHCO, N(CHO), CON $(COC_6H_5)$, $CH_2OCO.NH$, $N(COCH_3)$, $NHSO_2$, (E)-N=N, (Z)—N=N, (E)-N=CH, (E)-$N(CH_3)N$=CH, (E)- $CH_2ON$=N, (Z)-$CH_2ON$=CH, $CH(C_6H_5)$, $COCH_2O$, $COCH(CH_3)O$, $CH_2OCO$, $CH_2NHCO$, $CH_2SCO$, or $(C_6H_5)_2P^+CH_2Br^-$; q is 1; A, B and E are all H; D is H, hydroxy, halo, $C_{1-4}$ alkyl, $C_{1-4}$ alkoxy, nitro, cyano, trifluoromethyl, trifluoromethoxy, phenyl, phenoxy, amino or $CH_3O_2C.C$=$CH.OCH_3$; and G is H, halo, $C_{1-4}$ methyl, nitro; or D and G, when they are adjacent, join to form a benzene or pyridine ring.

In yet another aspect, the invention provides a compound having the formula (I.2), in which any two of K, L and M are nitrogen and the other is CB; X is oxygen or sulphur; Z is an optionally substituted 5- or 6-membered heterocyclic ring (excluding pyridine); and A, B and E are independently hydrogen, halogen (especially fluorine and chlorine), $C_{1-4}$ alkyl (especially methyl), $C_{1-4}$ alkoxy (especially methoxy), cyano, nitro or trifluoromethyl; and their N-oxides and N-alkyl salts.

In the formula (I.2), the pyrimidine ring containing K, L and M may be joined to the substituted phenoxy and —X—Z groups by any two of its ring carbon atoms adjacent to a ring nitrogen atom. The oxygen or sulphur atom X may join the heterocyclic ring Z at any of its ring atoms which valency allows.

The group Z may be any optionally substituted 5- or 6-membered heterocyclic ring except pyridine. The heterocyclic ring, which is suitably but not necessarily heteroaromatic, may be, for example, one of the following rings, in each case linked from any atom of the ring Z which valency allows: furan, thiophene, pyrrole, imidazole, pyrazole, thiazole, isothiazole, oxazole, isoxazole, 1,2,4-triazole, 1,2,3-triazole, 1,2,4-thiadiazole, 1,3,4-thiadiazole, pyrimidine, pyrazine, pyridazine, 1,2,4-triazine, 1,3,5-triazine, piperidine, morpholine, pyrrolidine or tetrahydrofuran.

Optional substituents of the heterocyclic ring Z include one or more of halogen, $C_{1-4}$ alkyl, $C_{3-6}$ cycloalkyl, $C_{2-4}$ alkenyl, $C_{2-4}$ alkynyl, $C_{2-4}$ alkenyloxy, $C_{2-4}$ alkynyloxy, phenyl, benzyloxy, cyano, isocyano, isothiocyanato, nitro, NR'R", NR'OR", $N_3$, NHCOR', NR'COR", NHCONR'R", N=CHNR'R", $NHSO_2R'$, OR', OCOR', $OSO_2R'$, SR', SOR', $SO_2R'$, $SO_2OR'$, $SO_2NR'R"$, COR', CR'=NOR", $CHR'CO_2R"$, $CO_2R'$, CONR'R", CSNR'R", $CH_3O_2C.C$:CH.O$CH_3$, 1-(imidazol-1-yl)vinyl, a 5-membered heterocyclic ring containing one, two or three nitrogen heteroatoms, or a 5- or 6-membered heterocyclic ring containing one or two oxygen or sulphur heteroatoms, optionally a nitrogen heteroatom and optionally one or two oxo or thioxo substituents; or two substituents when ortho to one another, join to form a 5- or 6-membered aliphatic or aromatic ring optionally containing one or more oxygen, sulphur or nitrogen atoms. R' and R" are independently hydrogen, $C_{1-4}$ alkyl, $C_{2-4}$ alkenyl or phenyl. The aliphatic moieties of any of the substituents may themselves be substituted with one or more of halogen, cyano, OR', SR', NR'R", $SiR'_3$ or OCOR' and the phenyl moieties of any of the substituents may themselves be substituted with one or more of halogen, $C_{1-4}$ alkyl, $C_{1-4}$ alkoxy, nitroor cyano.

Of particular interest are those compounds of formula (I.2) in which K and L are both nitrogen and H is CH.

The invention is illustrated by the compounds listed in Tables I to VI which follow. The compounds of Tables I to VI have the formulae (I.3) to (I.8), respectively, in which the values of A, B, Z, X and q are given in the tables. Throughout the tables the methyl 3-methoxypropenoate group has the (E)-configuration.

TABLE I (Formula I.3)

| Compound No | Z | X | q | A | B |
|---|---|---|---|---|---|
| 1 | $C_6H_5$ | S | 1 | H | H |
| 2 | $C_6H_5$ | SO | 1 | H | H |
| 3 | $C_6H_5$ | $SO_2$ | 1 | H | H |
| 4 | $C_6H_5$ | NH | 1 | H | H |
| 5 | $C_6H_5$ | $NCH_3$ | 1 | H | H |
| 6 | $C_6H_5$ | $NCH_2CH_3$ | 1 | H | H |
| 7 | $C_6H_5$ | $NCOCH_3$ | 1 | H | H |
| 8 | $C_6H_5$ | $NCH(CH_3)_2$ | 1 | H | H |
| 9 | $C_6H_5$ | $CH_2$ | 1 | H | H |
| 10 | $C_6H_5$ | $CH(CH_3)$ | 1 | H | H |
| 11 | $C_6H_5$ | $C(CH_3)_2$ | 1 | H | H |
| 12 | $C_6H_5$ | CO | 1 | H | H |
| 13 | $C_6H_5$ | $C=CH_2$ | 1 | H | H |
| 14 | $C_6H_5$ | $C=C(CH_3)_2$ | 1 | H | H |
| 15 | $C_6H_5$ | $CH_2CH_2$ | 1 | H | H |
| 16 | $C_6H_5$ | $CH(CH_3)CH_2$ | 1 | H | H |
| 17 | $C_6H_5$ | $CH_2CH(CH_3)$ | 1 | H | H |
| 18 | $C_6H_5$ | (E)-CH=CH | 1 | H | H |
| 19 | $C_6H_5$ | (E)-$C(CH_3)=C(CH_3)$ | 1 | H | H |
| 20 | $C_6H_5$ | C≡C | 1 | H | H |
| 21 | $C_6H_5$ | $OCH_2$ | 1 | H | H |
| 22 | $C_6H_5$ | $OCH(CH_3)$ | 1 | H | H |
| 23 | $C_6H_5$ | $CH_2O$ | 1 | H | H |
| 24 | $C_6H_5$ | $CH(CH_3)O$ | 1 | H | H |
| 25 | $C_6H_5$ | $SCH_2$ | 1 | H | H |
| 26 | $C_6H_5$ | $SCH(CH_3)$ | 1 | H | H |
| 27 | $C_6H_5$ | $S(O)CH_2$ | 1 | H | H |
| 28 | $C_6H_5$ | $S(O)CH(CH_3)$ | 1 | H | H |
| 29 | $C_6H_5$ | $S(O)_2CH_2$ | 1 | H | H |
| 30 | $C_6H_5$ | $S(O)_2CH(CH_3)$ | 1 | H | H |
| 31 | $C_6H_5$ | $CH_2S$ | 1 | H | H |
| 32 | $C_6H_5$ | $CH(CH_3)S$ | 1 | H | H |
| 33 | $C_6H_5$ | $CH_2S(O)$ | 1 | H | H |
| 34 | $C_6H_5$ | $CH(CH_3)S(O)$ | 1 | H | H |
| 35 | $C_6H_5$ | $CH_2S(O)_2$ | 1 | H | H |
| 36 | $C_6H_5$ | $CH(CH_3)S(O)_2$ | 1 | H | H |
| 37 | $C_6H_5$ | $NHCH_2$ | 1 | H | H |
| 38 | $C_6H_5$ | $N(CH_3)CH_2$ | 1 | H | H |
| 39 | $C_6H_5$ | $N(COCH_3)CH_2$ | 1 | H | H |
| 40 | $C_6H_5$ | $NHCH(CH_3)$ | 1 | H | H |
| 41 | $C_6H_5$ | $N(CH_3)CH(CH_3)$ | 1 | H | H |
| 42 | $C_6H_5$ | $N(COCH_3)CH(CH_3)$ | 1 | H | H |
| 43 | $C_6H_5$ | $CH_2NH$ | 1 | H | H |
| 44 | $C_6H_5$ | $CH_2N(CH_3)$ | 1 | H | H |
| 45 | $C_6H_5$ | $CH_2N(COCH_3)$ | 1 | H | H |
| 46 | $C_6H_5$ | $CH(CH_3)NH$ | 1 | H | H |
| 47 | $C_6H_5$ | $CH(CH_3)N(CH_3)$ | 1 | H | H |
| 48 | $C_6H_5$ | $CH(CH_3)N(COCH_3)$ | 1 | H | H |
| 49 | $C_6H_5$ | $CO_2$ | 1 | H | H |
| 50 | $C_6H_5$ | $O_2C$ | 1 | H | H |
| 51 | $C_6H_5$ | $SO_2O$ | 1 | H | H |
| 52 | $C_6H_5$ | $OSO_2$ | 1 | H | H |
| 53 | $C_6H_5$ | CO.CO | 1 | H | H |
| 54 | $C_6H_5$ | $COCH_2$ | 1 | H | H |
| 55 | $C_6H_5$ | $COCH(CH_3)$ | 1 | H | H |
| 56 | $C_6H_5$ | $CH_2CO$ | 1 | H | H |
| 57 | $C_6H_5$ | $CH(CH_3)CO$ | 1 | H | H |
| 58 | $C_6H_5$ | $CH(OH)CH_2$ | 1 | H | H |
| 59 | $C_6H_5$ | $CH(OH)CH(CH_3)$ | 1 | H | H |
| 60 | $C_6H_5$ | $CH_2CH(OH)$ | 1 | H | H |
| 61 | $C_6H_5$ | $CH(CH_3)CH(OH)$ | 1 | H | H |
| 62 | $C_6H_5$ | CONH | 1 | H | H |
| 63 | $C_6H_5$ | $CON(CH_3)$ | 1 | H | H |
| 64 | $C_6H_5$ | $CON(CH_2CH_2CH_3)$ | 1 | H | H |
| 65 | $C_6H_5$ | CON(CHO) | 1 | H | H |
| 66 | $C_6H_5$ | $CON(COCH_3)$ | 1 | H | H |
| 67 | $C_6H_5$ | NHCO | 1 | H | H |
| 68 | $C_6H_5$ | $N(CH_3)CO$ | 1 | H | H |
| 69 | $C_6H_5$ | $N(CH_2CH_3)CO$ | 1 | H | H |
| 70 | $C_6H_5$ | N(CHO)CO | 1 | H | H |
| 71 | $C_6H_5$ | $N(COCH_3)CO$ | 1 | H | H |
| 72 | $C_6H_5$ | $CSN(CH_3)$ | 1 | H | H |
| 73 | $C_6H_5$ | CSNH | 1 | H | H |
| 74 | $C_6H_5$ | NHCS | 1 | H | H |
| 75 | $C_6H_5$ | $N(CH_3)CS$ | 1 | H | H |

TABLE I-continued (Formula I.3)

| Compound No | Z | X | q | A | B |
|---|---|---|---|---|---|
| 76 | $C_6H_5$ | $SO_2NH$ | 1 | H | H |
| 77 | $C_6H_5$ | $SO_2N(CH_3)$ | 1 | H | H |
| 78 | $C_6H_5$ | $NHSO_2$ | 1 | H | H |
| 79 | $C_6H_5$ | $N(CH_3)SO_2$ | 1 | H | H |
| 80 | $C_6H_5$ | $N(CH_2CH_3)SO_2$ | 1 | H | H |
| 81 | $C_6H_5$ | $CS_2$ | 1 | H | H |
| 82 | $C_6H_5$ | $S_2C$ | 1 | H | H |
| 83 | $C_6H_5$ | COS | 1 | H | H |
| 84 | $C_6H_5$ | SCO | 1 | H | H |
| 85 | $C_6H_5$ | (E)-N=N | 1 | H | H |
| 86 | $C_6H_5$ | (E)-N=CH | 1 | H | H |
| 87 | $C_6H_5$ | (E)-N=C($CH_3$) | 1 | H | H |
| 88 | $C_6H_5$ | (E)-CH=N | 1 | H | H |
| 89 | $C_6H_5$ | (E)-C($CH_3$)=N | 1 | H | H |
| 90 | $C_6H_5$ | $CH_2CH_2CH_2$ | 1 | H | H |
| 91 | $C_6H_5$ | $CH(CH_3)CH_2CH_2$ | 1 | H | H |
| 92 | $C_6H_5$ | $CH_2CH(CH_3)CH_2$ | 1 | H | H |
| 93 | $C_6H_5$ | $CH_2CH_2CH(CH_3)$ | 1 | H | H |
| 94 | $C_6H_5$ | $OCH_2CH_2$ | 1 | H | H |
| 95 | $C_6H_5$ | $CH_2OCH_2$ | 1 | H | H |
| 96 | $C_6H_5$ | $CH_2CH_2O$ | 1 | H | H |
| 97 | $C_6H_5$ | $SCH_2CH_2$ | 1 | H | H |
| 98 | $C_6H_5$ | $S(O)CH_2CH_2$ | 1 | H | H |
| 99 | $C_6H_5$ | $S(O)_2CH_2CH_2$ | 1 | H | H |
| 100 | $C_6H_5$ | $CH_2SCH_2$ | 1 | H | H |
| 101 | $C_6H_5$ | $CH_2S(O)CH_2$ | 1 | H | H |
| 102 | $C_6H_5$ | $CH_2S(O)_2CH_2$ | 1 | H | H |
| 103 | $C_6H_5$ | $CH_2CH_2S$ | 1 | H | H |
| 104 | $C_6H_5$ | $CH_2CH_2S(O)$ | 1 | H | H |
| 105 | $C_6H_5$ | $CH_2CH_2S(O)_2$ | 1 | H | H |
| 106 | $C_6H_5$ | (E)-CH=NNH | 1 | H | H |
| 107 | $C_6H_5$ | (E)-C($CH_3$)=NNH | 1 | H | H |
| 108 | $C_6H_5$ | (E)-CH=NN($CH_3$) | 1 | H | H |
| 109 | $C_6H_5$ | (E)-NHN=CH | 1 | H | H |
| 110 | $C_6H_5$ | (E)-NHN=C($CH_3$) | 1 | H | H |
| 111 | $C_6H_5$ | (E)-N($CH_3$)N=CH | 1 | H | H |
| 112 | $C_6H_5$ | $CH_2CONH$ | 1 | H | H |
| 113 | $C_6H_5$ | $CH(CH_3)CON(CH_3)$ | 1 | H | H |
| 114 | $C_6H_5$ | $CH(CH_3)CON(CH_3)$ | 1 | H | H |
| 115 | $C_6H_5$ | (E)-CH=$CHCH_2O$ | 1 | H | H |
| 116 | $C_6H_5$ | $COCH_2CH_2O$ | 1 | H | H |
| 117 | $C_6H_5$ | * | 1 | H | H |
| 118 | $C_6H_5$ | * | 1 | H | H |
| 119 | 2-Cl—$C_6H_4$ | S | 1 | H | H |
| 120 | 3-Cl—$C_6H_4$ | N($CH_3$) | 1 | H | H |
| 121 | 4-Cl—$C_6H_4$ | NH | 1 | H | H |
| 122 | 2-F—$C_6H_4$ | $OCH_2$ | 1 | H | H |
| 123 | 3-F—$C_6H_4$ | $CH_2O$ | 1 | H | H |
| 124 | 4-F—$C_6H_4$ | S | 1 | H | H |
| 125 | 2-$CH_3$—$C_6H_4$ | N($CH_3$) | 1 | H | H |
| 126 | 3-$CH_3$—$C_6H_4$ | $CH_2$ | 1 | H | H |
| 127 | 4-$CH_3$—$C_6H_4$ | $OCH_2$ | 1 | H | H |
| 128 | 2-$CH_3O$—$C_6H_4$ | $CH_2O$ | 1 | H | H |
| 129 | 3-$CH_3O$—$C_6H_4$ | S | 1 | H | H |
| 130 | 4-$CH_3O$—$C_6H_4$ | N($CH_3$) | 1 | H | H |
| 131 | 2-$NO_2$—$C_6H_4$ | NH | 1 | H | H |
| 132 | 3-$NO_2$—$C_6H_4$ | $OCH_2$ | 1 | H | H |
| 133 | 4-$NO_2$—$C_6H_4$ | $CH_2O$ | 1 | H | H |
| 134 | 2-Cyano-$C_6H_4$ | S | 1 | H | H |
| 135 | 3-Cyano-$C_6H_4$ | N($CH_3$) | 1 | H | H |
| 136 | 4-Cyano-$C_6H_4$ | $CH_2$ | 1 | H | H |
| 137 | 2-Br—$C_6H_4$ | $OCH_2$ | 1 | H | H |
| 138 | 3-Br—$C_6H_5$ | $CH_2O$ | 1 | H | H |
| 139 | 4-Br—$C_6H_4$ | S | 1 | H | H |
| 140 | 2-$CF_3$—$C_6H_4$ | N($CH_3$) | 1 | H | H |
| 141 | 3-$CF_3$—$C_6H_4$ | NH | 1 | H | H |
| 142 | 4-$CF_3$—$C_6H_4$ | $OCH_2$ | 1 | H | H |
| 143 | 2-$C_6H_5O$—$C_6H_4$ | $CH_2O$ | 1 | H | H |
| 144 | 3-$C_6H_5O$—$C_6H_4$ | S | 1 | H | H |
| 145 | 4-$C_6H_5O$—$C_6H_4$ | N($CH_3$) | 1 | H | H |
| 146 | 2-$CH_3CH_2O$—$C_6H_4$ | $CH_2$ | 1 | H | H |
| 147 | 3-$CH_3CH_2O$—$C_6H_4$ | $OCH_2$ | 1 | H | H |
| 148 | 4-$CH_3CH_2O$—$C_6H_4$ | $CH_2O$ | 1 | H | H |
| 149 | 2-$C_6H_5$—$C_6H_4$ | S | 1 | H | H |
| 150 | 3-$C_6H_5$—$C_6H_4$ | N($CH_3$) | 1 | H | H |

TABLE I-continued (Formula I.3)

| Compound No | Z | X | q | A | B |
|---|---|---|---|---|---|
| 151 | 4-C$_6$H$_5$—C$_6$H$_4$ | NH | 1 | H | H |
| 152 | 2,3-di-Cl—C$_6$H$_3$ | OCH$_2$ | 1 | H | H |
| 153 | 2,4-di-Cl—C$_6$H$_3$ | CH$_2$O | 1 | H | H |
| 154 | 2,5-di-Cl—C$_6$H$_3$ | S | 1 | H | H |
| 155 | 2,6-di-Cl—C$_6$H$_3$ | N(CH$_3$) | 1 | H | H |
| 156 | 3,4-di-Cl—C$_6$H$_3$ | CH$_2$ | 1 | H | H |
| 157 | 3,5-di-Cl—C$_6$H$_3$ | OCH$_2$ | 1 | H | H |
| 158 | 2-Cl-3-CH$_3$O—C$_6$H$_3$ | CH$_2$O | 1 | H | H |
| 159 | 2-Cl-4-CH$_3$O—C$_6$H$_3$ | S | 1 | H | H |
| 160 | 2-Cl-5-CH$_3$O—C$_6$H$_3$ | N(CH$_3$) | 1 | H | H |
| 161 | 2-Cl-6-CH$_3$O—C$_6$H$_3$ | NH | 1 | H | H |
| 162 | 3-Cl-4-CH$_3$O—C$_6$H$_3$ | OCH$_2$ | 1 | H | H |
| 163 | 3-Cl-5-CH$_3$O—C$_6$H$_3$ | CH$_2$O | 1 | H | H |
| 164 | 2-CH$_3$O-3-Cl—C$_6$H$_3$ | S | 1 | H | H |
| 165 | 2-CH$_3$O-4-Cl—C$_6$H$_3$ | N(CH$_3$) | 1 | H | H |
| 166 | 2-CH$_3$O-5-Cl—C$_6$H$_3$ | CH$_2$ | 1 | H | H |
| 167 | 3-CH$_3$O-4-Cl—C$_6$H$_3$ | OCH$_2$ | 1 | H | H |
| 168 | 1-Naphthyl | CH$_2$O | 1 | H | H |
| 169 | 2-Naphthyl | S | 1 | H | H |
| 170 | 2-(E)-(CH$_3$O$_2$C.C=CH.OCH$_3$)C$_6$H$_4$ | N(CH$_3$) | 1 | H | H |
| 171 | " | NH | 1 | H | H |
| 172 | " | OCH$_2$ | 1 | H | H |
| 173 | " | CH$_2$O | 1 | H | H |
| 174 | " | S | 1 | H | H |
| 175 | C$_6$F$_5$ | N(CH$_3$) | 1 | H | H |
| 176 | 2,6-di-F—C$_6$H$_3$ | CH$_2$ | 1 | H | H |
| 177 | 2-Cyano-6-F—C$_6$H$_3$ | OCH$_2$ | 1 | H | H |
| 178 | 3-Cyano-4,6-di-F—C$_6$H$_2$ | CH$_2$O | 1 | H | H |
| 179 | 2,6-di-Cyano-C$_6$H$_3$ | S | 1 | H | H |
| 180 | C$_6$H$_5$ | — | 0 | H | H |
| 181 | 2-Cl—C$_6$H$_4$ | — | 0 | H | H |
| 182 | 3-F—C$_6$H$_4$ | — | 0 | H | H |
| 183 | 4-CH$_3$—C$_6$H$_4$ | — | 0 | H | H |
| 184 | 2-CH$_3$O—C$_6$H$_4$ | — | 0 | H | H |
| 185 | 2,6-di-F—C$_6$H$_4$ | — | 0 | H | H |
| 186 | Pyridin-2-yl | — | 0 | H | H |
| 187 | Pyridin-3-yl | — | 0 | H | H |
| 188 | Pyridin-4-yl | — | 0 | H | H |
| 189 | Pyrimidin-2-yl | — | 0 | H | H |
| 190 | Pyrimidin-4-yl | — | 0 | H | H |
| 191 | Pyrimdin-5-yl | — | 0 | H | H |
| 192 | 1,2,4-Triazin-3-yl | — | 0 | H | H |
| 193 | 1,3,5-Triazin-2-yl | — | 0 | H | H |
| 194 | Pyrazin-2-yl | — | 0 | H | H |
| 195 | Pyridazin-3-yl | — | 0 | H | H |
| 196 | Pyridazin-4-yl | — | 0 | H | H |
| 197 | Quinolin-2-yl | — | 0 | H | H |
| 198 | Benzoxazol-2-yl | — | 0 | H | H |
| 199 | Benzthiazol-2-yl | — | 0 | H | H |
| 200 | Thien-2-yl | — | 0 | H | H |
| 201 | Thien-3-yl | — | 0 | H | H |
| 202 | 5-CF$_3$-Pyridin-2-yl | — | 0 | H | H |
| 203 | 3-F-Pyridin-2-yl | — | 0 | H | H |
| 204 | 3-Cl-Pyridin-2-yl | — | 0 | H | H |
| 205 | 4-Br-Pyridin-2-yl | — | 0 | H | H |
| 206 | 5-CH$_3$-Pyridin-2-yl | — | 0 | H | H |
| 207 | 6-CH$_3$O-Pyridin-2-yl | — | 0 | H | H |
| 208 | 2-F-Pyridin-3-yl | — | 0 | H | H |
| 209 | 3-CF$_3$-Pyridin-4-yl | — | 0 | H | H |
| 210 | C$_6$H$_5$ | — | 0 | Cl | H |
| 211 | C$_6$H$_5$ | N(CH$_3$) | 1 | Cl | H |
| 212 | C$_6$H$_5$ | NH | 1 | CH$_3$O | H |
| 213 | C$_6$H$_5$ | OCH$_2$ | 1 | CH$_3$S | H |
| 214 | C$_6$H$_5$ | CH$_2$O | 1 | NH$_2$ | H |
| 215 | C$_6$H$_5$ | S | 1 | H | F |
| 216 | C$_6$H$_5$ | N(CH$_3$) | 1 | H | Cl |
| 217 | C$_6$H$_5$ | CH$_2$ | 1 | H | CH$_3$ |
| 218 | Pyridin-2-yl | S | 1 | H | H |
| 219 | Pyridin-2-yl | N(CH$_3$) | 1 | H | H |
| 220 | Pyridin-2-yl | NH | 1 | H | H |
| 221 | Pyridin-2-yl | OCH$_2$ | 1 | H | H |
| 222 | Pyridin-2-yl | CH$_2$O | 1 | H | H |
| 223 | Pyridin-2-yl | CH$_2$CH$_2$O | 1 | H | H |
| 224 | Pyridin-2-yl | CH$_2$CH$_2$CH$_2$O | 1 | H | H |
| 225 | Pyridin-3-yl | S | 1 | H | H |

TABLE I-continued (Formula I.3)

| Compound No | Z | X | q | A | B |
|---|---|---|---|---|---|
| 226 | Pyridin-3-yl | N(CH$_3$) | 1 | H | H |
| 227 | Pyridin-3-yl | NH | 1 | H | H |
| 228 | Pyridin-3-yl | OCH$_2$ | 1 | H | H |
| 229 | Pyridin-3-yl | CH$_2$O | 1 | H | H |
| 230 | Pyridin-3-yl | CH$_2$CH$_2$O | 1 | H | H |
| 231 | Pyridin-3-yl | CH$_2$CH$_2$CH$_2$O | 1 | H | H |
| 232 | Pyridin-4-yl | S | 1 | H | H |
| 233 | Pyridin-4-yl | N(CH$_3$) | 1 | H | H |
| 234 | Pyridin-4-yl | NH | 1 | H | H |
| 235 | Pyridin-4-yl | OCH$_2$ | 1 | H | H |
| 236 | Pyridin-4-yl | CH$_2$O | 1 | H | H |
| 237 | Pyridin-4-yl | CH$_2$CH$_2$O | 1 | H | H |
| 238 | Pyridin-4-yl | CH$_2$CH$_2$CH$_2$O | 1 | H | H |
| 239 | Pyrimidin-2-yl | S | 1 | H | H |
| 240 | Pyrimidin-2-yl | N(CH$_3$) | 1 | H | H |
| 241 | Pyrimidin-2-yl | NH | 1 | H | H |
| 242 | Pyrimidin-2-yl | OCH$_2$ | 1 | H | H |
| 243 | Pyrimidin-2-yl | CH$_2$O | 1 | H | H |
| 244 | Pyrimidin-2-yl | CH$_2$CH$_2$O | 1 | H | H |
| 245 | Pyrimidin-2-yl | CH$_2$CH$_2$CH$_2$O | 1 | H | H |
| 246 | Pyrimidin-4-yl | S | 1 | H | H |
| 247 | Pyrimidin-4-yl | N(CH$_3$) | 1 | H | H |
| 248 | Pyrimidin-4-yl | NH | 1 | H | H |
| 249 | Pyrimidin-4-yl | OCH$_2$ | 1 | H | H |
| 250 | Pyrimidin-4-yl | CH$_2$O | 1 | H | H |
| 251 | Pyrimidin-4-yl | CH$_2$CH$_2$O | 1 | H | H |
| 252 | Pyrimidin-4-yl | CH$_2$CH$_2$CH$_2$O | 1 | H | H |
| 253 | Pyrimidin-5-yl | S | 1 | H | H |
| 254 | Pyrimidin-5-yl | N(CH$_3$) | 1 | H | H |
| 255 | Pyrimidin-5-yl | NH | 1 | H | H |
| 256 | Pyrimidin-5-yl | OCH$_2$ | 1 | H | H |
| 257 | Pyrimidin-5-yl | CH$_2$O | 1 | H | H |
| 256 | Pyrimidin-5-yl | CH$_2$CH$_2$O | 1 | H | H |
| 259 | Pyrimidin-5-yl | CH$_2$CH$_2$CH$_2$O | 1 | H | H |
| 260 | Pyrazin-2-yl | S | 1 | H | H |
| 261 | Pyrazin-2-yl | N(CH$_3$) | 1 | H | H |
| 262 | Pyrazin-2-yl | NH | 1 | H | H |
| 263 | Pyrazin-2-yl | OCH$_2$ | 1 | H | H |
| 264 | Pyrazin-2-yl | CH$_2$O | 1 | H | H |
| 265 | Pyrazin-2-yl | CH$_2$CH$_2$O | 1 | H | H |
| 266 | Pyrazin-2-yl | CH$_2$CH$_2$CH$_2$O | 1 | H | H |
| 267 | Pyridazin-3-yl | S | 1 | H | H |
| 268 | Pyridazin-3-yl | N(CH$_3$) | 1 | H | H |
| 269 | Pyridazin-3-yl | NH | 1 | H | H |
| 270 | Pyridazin-3-yl | OCH$_2$ | 1 | H | H |
| 271 | Pyridazin-3-yl | CH$_2$O | 1 | H | H |
| 272 | Pyridazin-3-yl | CH$_2$CH$_2$O | 1 | H | H |
| 273 | Pyridazin-3-yl | CH$_2$CH$_2$CH$_2$O | 1 | H | H |
| 274 | Pyridazin-4-yl | S | 1 | H | H |
| 275 | Pyridazin-4-yl | N(CH$_3$) | 1 | H | H |
| 276 | Pyridazin-4-yl | NH | 1 | H | H |
| 277 | Pyridazin-4-yl | OCH$_2$ | 1 | H | H |
| 278 | Pyridazin-4-yl | CH$_2$O | 1 | H | H |
| 279 | Pyridazin-4-yl | CH$_2$CH$_2$O | 1 | H | H |
| 280 | Pyridazin-4-yl | CH$_2$CH$_2$CH$_2$O | 1 | H | H |
| 281 | 1,2,4-Triazin-3-yl | S | 1 | H | H |
| 282 | 1,2,4-Triazin-3-yl | N(CH$_3$) | 1 | H | H |
| 283 | 1,2,4-Triazin-5-yl | NH | 1 | H | H |
| 284 | 1,2,4-Triazin-5-yl | OCH$_2$ | 1 | H | H |
| 285 | 1,2,4-Triazin-6-yl | CH$_2$O | 1 | H | H |
| 286 | 1,2,4-Triazin-6-yl | CH$_2$CH$_2$O | 1 | H | H |
| 287 | 1,3,5-Triazin-2-yl | CH$_2$CH$_2$CHO | 1 | H | H |
| 288 | 1,3,5-Triazin-2-yl | S | 1 | H | H |
| 289 | 1,3,5-Triazin-2-yl | N(CH$_3$) | 1 | H | H |
| 290 | Quinolin-2-yl | NH | 1 | H | H |
| 291 | Quinolin-2-yl | OCH$_2$ | 1 | H | H |
| 292 | Quinolin-2-yl | CH$_2$O | 1 | H | H |
| 293 | Isoquinolin-1-yl | CH$_2$CH$_2$O | 1 | H | H |
| 294 | Isoquinolin-1-yl | CH$_2$CH$_2$CH$_2$O | 1 | H | H |
| 295 | Isoquinolin-1-yl | S | 1 | H | H |
| 296 | Benzoxazol-2-yl | N(CH$_3$) | 1 | H | H |
| 297 | Benzoxazol-2-yl | NH | 1 | H | H |
| 298 | Benzoxazol-2-yl | OCH$_2$ | 1 | H | H |
| 299 | Benzthiazol-2-yl | CH$_2$O | 1 | H | H |
| 300 | Benzthiazol-2-yl | CH$_2$CH$_2$O | 1 | H | H |

TABLE I-continued (Formula I.3)

| Compound No | Z | X | q | A | B |
|---|---|---|---|---|---|
| 301 | Benzthiazol-2-yl | $CH_2CH_2CH_2O$ | 1 | H | H |
| 302 | Thien-2-yl | S | 1 | H | H |
| 303 | Thien-2-yl | $N(CH_3)$ | 1 | H | H |
| 304 | Thien-2-yl | NH | 1 | H | H |
| 305 | Thien-3-yl | $OCH_2$ | 1 | H | H |
| 306 | Thien-3-yl | $CH_2O$ | 1 | H | H |
| 307 | Thien-3-yl | $CH_2CH_2O$ | 1 | H | H |
| 308 | 1,2,4-Triazol-1-yl | $CH_2CH_2CH_2O$ | 1 | H | H |
| 309 | Quinazolin-4-yl | S | 1 | H | H |
| 310 | Quinazolin-4-yl | $N(CH_3)$ | 1 | H | H |
| 311 | Quinolin-4-yl | NH | 1 | H | H |
| 312 | Quinolin-4-yl | $OCH_2$ | 1 | H | H |
| 313 | Purin-6-yl | $CH_2O$ | 1 | H | H |
| 314 | Thiazol-2-yl | $CH_2CH_2O$ | 1 | H | H |
| 315 | Thiazol-2-yl | $CH_2CH_2CH_2O$ | 1 | H | H |
| 316 | Thiazol-4-yl | S | 1 | H | H |
| 317 | Thiazol-4-yl | $N(CH_3)$ | 1 | H | H |
| 318 | Thiazol-5-yl | NH | 1 | H | H |
| 319 | Thiazol-5-yl | $OCH_2$ | 1 | H | H |
| 320 | Furan-2-yl | $CH_2O$ | 1 | H | H |
| 321 | N—$CH_3$-Pyrrol-2-yl | $CH_2CH_2O$ | 1 | H | H |
| 322 | N—$CH_3$-Pyrrol-2-yl | $CH_2CH_2CH_2O$ | 1 | H | H |
| 323 | 5-$CF_3$-Pyridin-2-yl | S | 1 | H | H |
| 324 | 3-F-Pyridin-2-yl | $N(CH_3)$ | 1 | H | H |
| 325 | 3-Cl-Pyridin-2-yl | NH | 1 | H | H |
| 326 | 4-Br-Pyridin-2-yl | $OCH_2$ | 1 | H | H |
| 327 | 3-$CH_3$-Pyridin-2-yl | $CH_2O$ | 1 | H | H |
| 328 | 6-$CH_3O$-Pyridin-2-yl | $CH_2CH_2O$ | 1 | H | H |
| 329 | 4,6-di-F-Pyridin-2-yl | $CH_2CH_2CH_2O$ | 1 | H | H |
| 330 | 2-Cl-Pyridin-3-yl | S | 1 | H | H |
| 331 | 2-$CH_3O$-Pyridin-3yl | $N(CH_3)$ | 1 | H | H |
| 332 | 2-Cl-Pyridin-4-yl | NH | 1 | H | H |
| 333 | 4-Cl-Pyrimidin-2-yl | $OCH_2$ | 1 | H | H |
| 334 | 4-Cyanopyrimidin-2-yl | $CH_2O$ | 1 | H | H |
| 335 | 4-$CH_3$-Pyrimidin-2-yl | $CH_2CH_2O$ | 1 | H | H |
| 336 | 5-$CH_3$-Pyrimidin-2-yl | $CH_2CH_2CH_2O$ | 1 | H | H |
| 337 | 5-Cyanopyrimidin-2-yl | S | 1 | H | H |
| 338 | 5-F-Pyrimidin-2-yl | $N(CH_3)$ | 1 | H | H |
| 339 | 2-Cl-Pyrimidin-4-yl | NH | 1 | H | H |
| 340 | 2-$CH_3$-Pyrimidin-4-yl | $OCH_2$ | 1 | H | H |
| 341 | 2-$CH_3S$-Pyrimidin-4-yl | $CH_2O$ | 1 | H | H |
| 342 | 6-Cl-Pyrazin-2-yl | $CH_2CH_2O$ | 1 | H | H |
| 343 | 6-Cl-Pyridazin-3-yl | $CH_2CH_2CH_2O$ | 1 | H | H |
| 344 | 6-Cl-Pyridazin-3-yl | S | 1 | H | H |
| 345 | 2-$CH_3$-Thiazol-4-yl | $N(CH_3)$ | 1 | H | H |
| 346 | 5-$CF_3$-1,3,4-Thiadiazol-2-yl | NH | 1 | H | H |
| 347 | 4-Cl-1,2,5-Thiadiazol-3-yl | $OCH_2$ | 1 | H | H |
| 348 | Pyrimidin-2-yl,1-N-oxide | $CH_2O$ | 1 | H | H |
| 349 | Pyrimidin-4-yl,1-N-oxide | $CH_2CH_2O$ | 1 | H | H |
| 350 | Pyrimidin-4-yl,3-N-oxide | $CH_2CH_2CH_2O$ | 1 | H | H |
| 351 | Pyridin-2-yl,1-N-oxide | S | 1 | H | H |
| 352 | Pyrazin-2-yl,1-N-oxide | $N(CH_3)$ | 1 | H | H |
| 353 | * | NH | 1 | H | H |
| 354 | 2-Cyano-$C_6H_4$ | $N(CH_3)$ | 1 | H | H |
| 355 | Pyridin-2-yl | SO | 1 | H | H |
| 356 | Pyridin-2-yl | $SO_2$ | 1 | H | H |
| 357 | 2-Cyano-$C_6H_4$ | $CH_2CH_2O$ | 1 | H | H |
| 358 | 2-$NO_2$—$C_6H_4$ | $CH_2CH_2O$ | 1 | H | H |
| 359 | 4-Cyano-$C_6H_4$ | $CH_2CH_2O$ | 1 | H | H |
| 360 | $C_6H_5$ | $CH_2CH_2CH_2O$ | 1 | H | H |
| 361 | 2-$NO_2$—$C_6H_5$ | $CH_2CH_2CH_2O$ | 1 | H | H |
| 362 | 2-HO—$C_6H_4$ | CONH | 1 | H | H |
| 363 | 2-$CF_3$—$C_6H_4$ | $CH_2CH_2O$ | 1 | H | H |
| 364 | 2-$CH_3$—$C_6H_4$ | $CH_2CH_2O$ | 1 | H | H |
| 365 | 2-$CH_3O$—$C_6H_4$ | $CH_2CH_2O$ | 1 | H | H |
| 366 | 2-F—$C_6H_4$ | $CH_2CH_2O$ | 1 | H | H |
| 367 | 2-HO—$C_6H_5$ | CSNH | 1 | H | H |
| 368 | 2-Cl—$C_6H_4$ | $CH_2CH_2O$ | 1 | H | H |
| 369 | $C_6H_5$ | $CH(CN)O$ | 1 | H | H |
| 370 | 2,6-di-F—$C_6H_3$ | $CH_2CH_2O$ | 1 | H | H |
| 371 | $C_6H_5$ | $CH(CF_3)O$ | 1 | H | H |
| 372 | 2-Cl-6-F—$C_6H_3$ | $CH_2CH_2O$ | 1 | H | H |
| 373 | 2,6-di-Cl—$C_6H_5$ | $CH_2CH_2O$ | 1 | H | H |
| 374 | 2,6-di-F—$C_6H_3$ | $CH_2O$ | 1 | H | H |
| 375 | 2-$NO_2$—$C_6H_4$ | $CH_2O$ | 1 | H | H |

TABLE I-continued (Formula I.3)

| Compound No | Z | X | q | A | B |
|---|---|---|---|---|---|
| 376 | C$_6$H$_5$ | (E)-CH=CHCH$_2$O | 1 | H | H |
| 377 | 2-Cyano-C$_6$H$_4$ | NH | 1 | H | H |
| 378 | C$_6$H$_5$ | — | 0 | Cl | H |
| 379 | 2-HO—C$_6$H$_4$ | NH | 1 | H | H |
| 380 | 2-(CH$_3$O)—C$_6$H$_4$ | NH | 1 | H | H |
| 381 | 2-Cyano-C$_6$H$_4$ | SO$_2$O | 1 | H | H |
| 382 | 2,6-di-F—C$_6$H$_3$ | OCH$_2$CH$_2$O | 1 | H | H |
| 383 | 2-Cl-6-CF$_3$—C$_6$H$_3$ | CH$_2$O | 1 | H | H |
| 384 | 2-Cl—C$_6$H$_4$ | CH$_2$CH$_2$CH$_2$O | 1 | H | H |
| 385 | 2-CF$_3$—C$_6$H$_4$ | CH$_2$O | 1 | H | H |
| 386 | 2-F-6-Cl—C$_6$H$_3$ | CH$_2$O | 1 | H | H |
| 387 | C$_6$H$_5$ | C≡CCH$_2$O | 1 | H | H |
| 388 | C$_6$F$_5$ | CH$_2$O | 1 | H | H |
| 389 | 2-Cyano-C$_6$H$_4$ | CH$_2$O | 1 | H | H |
| 390 | 4-Cyano-C$_6$H$_4$ | OCH$_2$CH$_2$O | 1 | H | H |
| 391 | C$_6$H$_5$ | SCH$_2$CH$_2$O | 1 | H | H |
| 392 | 2-HO—C$_6$H$_4$ | N(CHO) | 1 | H | H |
| 393 | 2-Cyano-C$_6$H$_4$ | SCH$_2$CH$_2$O | 1 | H | H |
| 394 | Thien-2-yl | CH$_2$O | 1 | H | H |
| 395 | 2-Cyano-C$_6$H$_4$ | (E)-CH=CHCH$_2$O | 1 | H | H |
| 396 | 2-Cyano-C$_6$H$_4$ | OCH$_2$CH$_2$O | 1 | H | H |
| 397 | 2-Cyano-6-F—C$_6$H$_3$ | OCH$_2$CH$_2$O | 1 | H | H |
| 398 | C$_6$H$_5$ | CON(COC$_6$H$_5$) | 1 | H | H |
| 399 | 2-(2-HO—C$_6$H$_4$)-4-CH$_3$-Thiazol-5-yl | — | 0 | H | H |
| 400 | 2-NH$_2$-Benzofuran-3-yl | — | 0 | H | H |
| 401 | 2-CH$_3$CH$_2$O—C$_6$H$_4$ | NH | 1 | H | H |
| 402 | 2-CH$_3$(CH$_2$)$_3$O—C$_6$H$_4$ | NH | 1 | H | H |
| 403 | C$_6$H$_5$ | (E)-C(CH$_3$)=NO | 1 | H | H |
| 404 | 2-Pyrazinyl | (E)-C(CH$_3$)=NO | 1 | H | H |
| 405 | 4-F—C$_6$H$_4$ | CH$_2$O | 1 | H | H |
| 406 | 3-CF$_3$—C$_6$H$_4$ | (E)-C(NH$_2$)=NO | 1 | H | H |
| 407 | Pyrrol-2-yl | (E)-C(CH$_3$)=NO | 1 | H | H |
| 408 | Imidazol-2-yl | S | 1 | H | H |
| 409 | 5-CF$_3$-4-CH$_3$-1,2,4-Triazol-3-yl | S | 1 | H | H |
| 410 | Isoquinolin-4-yl | O | 1 | H | H |
| 411 | 4-Cyano-5-CH$_3$S-isothiazol-3-yl | O | 1 | H | H |
| 412 | 1,2,4-Triazol-3-yl | S | 1 | H | H |
| 413 | 5-CF$_3$-1,2,4-Triazol-3-yl | S | 1 | H | H |
| 414 | 5-t-Butyl-1,2,4-Triazol-3-yl | S | 1 | H | H |
| 415 | 1,2,5-Thiadiazol-3-yl | O | 1 | H | H |
| 416 | N—CH$_3$-Pyrrolidin-3-yl | O | 1 | H | H |
| 417 | Δ$^2$-Thiazolin-2-yl | S | 1 | H | H |
| 418 | * | S | 1 | H | H |
| 419 | Piperidin-4-yl | O | 1 | H | H |
| 420 | Tetrahydropyran-4-yl | O | 1 | H | H |
| 421 | * | S | 1 | H | H |
| 422 | Furan-2-yl | O | 1 | H | H |
| 423 | Furan-2-yl | S | 1 | H | H |
| 424 | Furan-3-yl | O | 1 | H | H |
| 425 | Furan-3-yl | S | 1 | H | H |
| 426 | Thien-3-yl | S | 1 | H | H |
| 427 | 3-Cl-Thien-2-yl | O | 1 | H | H |
| 428 | 4-Cl-Thien-2-yl | S | 1 | H | H |
| 429 | 5-Cl-Thien-2-yl | O | 1 | H | H |
| 430 | 5-Cl-Thien-2-yl | S | 1 | H | H |
| 431 | 5-Br-Thien-2-yl | O | 1 | H | H |
| 432 | 5-Br-Thien-2-yl | S | 1 | H | H |
| 433 | 5-NO$_2$-Thien-2-yl | O | 1 | H | H |
| 434 | 5-NO$_2$-Thien-2-yl | S | 1 | H | H |
| 435 | 2-Cl-Thien-3-yl | O | 1 | H | H |
| 436 | 2-Cl-Thien-4-yl | S | 1 | H | H |
| 437 | 2-Br-Thien-4-yl | O | 1 | H | H |
| 438 | 2-Br-Thien-4-yl | S | 1 | H | H |
| 439 | N—CH$_3$-Pyrrol-3-yl | O | 1 | H | H |
| 440 | N—CH$_3$-Pyrrol-3-yl | S | 1 | H | H |
| 441 | N—CH$_3$-Pyrrol-2-yl | O | 1 | H | H |
| 442 | N—CH$_3$-Pyrrol-2-yl | S | 1 | H | H |
| 443 | Benzofuran-2-yl | O | 1 | H | H |
| 444 | Benzofuran-2-yl | S | 1 | H | H |
| 445 | Benzofuran-3-yl | O | 1 | H | H |
| 446 | Benzofuran-3-yl | S | 1 | H | H |
| 447 | Benzothiophen-2-yl | O | 1 | H | H |
| 448 | Benzothiophen-2-yl | S | 1 | H | H |
| 449 | Benzothiophen-3-yl | O | 1 | H | H |

TABLE I-continued (Formula I.3)

| Compound No | Z | X | q | A | B |
|---|---|---|---|---|---|
| 450 | Benzothiophen-3-yl | S | 1 | H | H |
| 451 | Pyrrol-2-yl | O | 1 | H | H |
| 452 | Pyrrol-2-yl | S | 1 | H | H |
| 453 | Pyrrol-3-yl | O | 1 | H | H |
| 454 | Pyrrol-3-yl | S | 1 | H | H |
| 455 | Indol-2-yl | O | 1 | H | H |
| 456 | Indol-2-yl | S | 1 | H | H |
| 457 | Indol-3-yl | O | 1 | H | H |
| 458 | Indol-3-yl | S | 1 | H | H |
| 459 | N—CH$_3$-Indol-2-yl | O | 1 | H | H |
| 460 | N—CH$_3$-Indol-2-yl | S | 1 | H | H |
| 461 | N—CH$_3$-Indol-3-yl | O | 1 | H | H |
| 462 | N—CH$_3$-Indol-3-yl | S | 1 | H | H |
| 463 | N—CH$_3$-Pyrazol-3-yl | O | 1 | H | H |
| 464 | N—CH$_3$-Pyrazol-3-yl | S | 1 | H | H |
| 465 | N—CH$_3$-Pyrazol-4-yl | O | 1 | H | H |
| 466 | N—CH$_3$-Pyrazol-4-yl | S | 1 | H | H |
| 467 | N—CH$_3$-Pyrazol-5-yl | O | 1 | H | H |
| 468 | N—CH$_3$-Pyrazol-5-yl | S | 1 | H | H |
| 469 | Isoxazol-3-yl | O | 1 | H | H |
| 470 | Isoxazol-3-yl | S | 1 | H | H |
| 471 | Isoxazol-4-yl | O | 1 | H | H |
| 472 | Isoxazol-4-yl | S | 1 | H | H |
| 473 | Isoxazol-5-yl | O | 1 | H | H |
| 474 | Isoxazol-5-yl | S | 1 | H | H |
| 475 | Isothiazol-3-yl | O | 1 | H | H |
| 476 | Isothiazol-3-yl | S | 1 | H | H |
| 477 | Isothiazol-4-yl | O | 1 | H | H |
| 478 | Isothiazol-4-yl | S | 1 | H | H |
| 479 | Isothiazol-5-yl | O | 1 | H | H |
| 480 | Isothiazol-5-yl | S | 1 | H | H |
| 481 | Oxazol-2-yl | O | 1 | H | H |
| 482 | Oxazol-2-yl | S | 1 | H | H |
| 483 | Oxazol-4-yl | O | 1 | H | H |
| 484 | Oxazol-4-yl | S | 1 | H | H |
| 485 | Oxazol-5-yl | O | 1 | H | H |
| 486 | Oxazol-5-yl | S | 1 | H | H |
| 487 | Thiazol-2-yl | O | 1 | H | H |
| 488 | Thiazol-2-yl | S | 1 | H | H |
| 489 | Thiazol-4-yl | O | 1 | H | H |
| 490 | Thiazol-4-yl | S | 1 | H | H |
| 491 | Thiazol-5-yl | O | 1 | H | H |
| 492 | Thiazol-5-yl | S | 1 | H | H |
| 493 | N—CH$_3$-Imidazol-2-yl | O | 1 | H | H |
| 494 | N—CH$_3$-Imidazol-2-yl | S | 1 | H | H |
| 495 | N—CH$_3$-Imidazol-4-yl | O | 1 | H | H |
| 496 | N—CH$_3$-Imidazol-4-yl | S | 1 | H | H |
| 497 | N—CH$_3$-Imidazol-5-yl | O | 1 | H | H |
| 498 | N—CH$_3$-Imidazol-5-yl | S | 1 | H | H |
| 499 | 1,2-Benzisoxazol-3-yl | O | 1 | H | H |
| 500 | 1,2-Benzisoxazol-3-yl | S | 1 | H | H |
| 501 | 1,2-Benzisothiazol-3-yl | O | 1 | H | H |
| 502 | 1,2-Benzisothiazol-3-yl | S | 1 | H | H |
| 503 | 1-CH$_3$-Indazol-3-yl | O | 1 | H | H |
| 504 | 1-CH$_3$-Indazol-3-yl | S | 1 | H | H |
| 505 | 5-Cl-Benzoxazol-2-yl | O | 1 | H | H |
| 506 | 5-Cl-Benzoxazol-2-yl | S | 1 | H | H |
| 507 | 6-F-Benzoxazol-2-yl | O | 1 | H | H |
| 508 | 6-F-Benzoxazol-2-yl | S | 1 | H | H |
| 509 | 5-F-Benzthiazol-2-yl | O | 1 | H | H |
| 510 | 5-F-Benzthiazol-2-yl | S | 1 | H | H |
| 511 | 6-F-Benzthiazol-2-yl | O | 1 | H | H |
| 512 | 6-F-Benzthiazol-2-yl | S | 1 | H | H |
| 513 | * | O | 1 | H | H |
| 514 | * | S | 1 | H | H |
| 515 | * | O | 1 | H | H |
| 516 | * | S | 1 | H | H |
| 517 | 1-CH$_3$-1,2,3-Triazol-4-yl | O | 1 | H | H |
| 518 | 1-CH$_3$-1,2,3-Triazol-4-yl | S | 1 | H | H |
| 519 | 1-CH$_3$-1,2,3-Triazol-5-yl | O | 1 | H | H |
| 520 | 1-CH$_3$-1,2,3-Triazol-5-yl | S | 1 | H | H |
| 521 | 1-CH$_3$-1,2,4-Triazol-3-yl | O | 1 | H | H |
| 522 | 1-CH$_3$-1,2,4-Triazol-3-yl | S | 1 | H | H |
| 523 | 1-CH$_3$-1,2,4-Triazol-5-yl | O | 1 | H | H |
| 524 | 1-CH$_3$-1,2,4-Triazol-5-yl | S | 1 | H | H |

TABLE I-continued (Formula I.3)

| Compound No | Z | X | q | A | B |
|---|---|---|---|---|---|
| 525 | 1-CH$_3$-Tetrazol-5-yl | O | 1 | H | H |
| 526 | 1-CH$_3$-Tetrazol-5-yl | S | 1 | H | H |
| 527 | 2-CH$_3$-Tetrazol-5-yl | O | 1 | H | H |
| 528 | 2-CH$_3$-Tetrazol-5-yl | S | 1 | H | H |
| 529 | Benzoxazol-2-yl | O | 1 | H | H |
| 530 | Benzthiazol-2-yl | S | 1 | H | H |
| 531 | 5-CF$_3$-1,3,4-Thiadiazol-2-yl | O | 1 | H | H |
| 532 | 5-CF$_3$-1,3,4-Thiadiazol-2-yl | S | 1 | H | H |
| 533 | 6-Cl-Benzoxazol-2-yl | O | 1 | H | H |
| 534 | 6-Cl-Benzoxazol-2-yl | S | 1 | H | H |
| 535 | 5-F-Benzoxazol-2-yl | O | 1 | H | H |
| 536 | 5-F-Benzoxazol-2-yl | S | 1 | H | H |
| 537 | 5-NO$_2$-Thiazol-2-yl | O | 1 | H | H |
| 538 | 5-NO$_2$-Thiazol-2-yl | S | 1 | H | H |
| 539 | 6-Cl-Pyrazin-2-yl | O | 1 | H | H |
| 540 | 6-Cl-Pyrazin-2-yl | S | 1 | H | H |
| 541 | 3-Cl-Pyrazin-2-yl | O | 1 | H | H |
| 542 | 5-Cl-Pyrazin-2-yl | S | 1 | H | H |
| 543 | 6-Br-Pyrazin-2-yl | O | 1 | H | H |
| 544 | 6-Br-Pyrazin-2-yl | S | 1 | H | H |
| 545 | 5-Br-Pyrazin-2-yl | O | 1 | H | H |
| 546 | 5-Br-Pyrazin-2-yl | S | 1 | H | H |
| 547 | Quinoxalin-2-yl | O | 1 | H | H |
| 548 | Quinoxalin-2-yl | S | 1 | H | H |
| 549 | 6-Cl-Pyridazin-3-yl | O | 1 | H | H |
| 550 | 6-Cl-Pyridazln-3-yl | S | 1 | H | H |
| 551 | 5-Cl-Pyridazin-3-yl | O | 1 | H | H |
| 552 | 5-Cl-Pyridazin-3-yl | S | 1 | H | H |
| 553 | 6-Br-Pyridazin-3-yl | O | 1 | H | H |
| 554 | 6-Br-Pyridazin-3-yl | S | 1 | H | H |
| 555 | 5-Br-Pyridazin-3-yl | O | 1 | H | H |
| 556 | 5-Br-Pyridazin-3-yl | S | 1 | H | H |
| 557 | 3-Cl-Pyridazin-5-yl | O | 1 | H | H |
| 558 | 3-Cl-Pyridazin-5-yl | S | 1 | H | H |
| 559 | 3-Br-Pyridazin-5-yl | O | 1 | H | H |
| 560 | 3-Br-Pyridazin-5-yl | S | 1 | H | H |
| 561 | Cinnolin-3-yl | O | 1 | H | H |
| 562 | Clnnolin-3-yl | S | 1 | H | H |
| 563 | 1,2,3-Triazin-4-yl | O | 1 | H | H |
| 564 | 1,2,3-Triazin-4-yl | S | 1 | H | H |
| 565 | 6-Cl-1,2,3-Triazin-4-yl | O | 1 | H | H |
| 566 | 6-Cl-1,2,3-Triazin-4-yl | S | 1 | H | H |
| 567 | 6-Br-1,2,3-Triazin-4-yl | O | 1 | H | H |
| 568 | 6-Br-1,2,3-Triazin-4-yl | S | 1 | H | H |
| 569 | 1,2,3-Triazin-5-yl | O | 1 | H | H |
| 570 | 1,2,3-Triazin-5-yl | S | 1 | H | H |
| 571 | 6-Cl-1,2,4-Triazin-3-yl | O | 1 | H | H |
| 572 | 6-Cl-1,2,4-Triazin-3-yl | S | 1 | H | H |
| 573 | 5-Cl-1,2,4-Triazin-3-yl | O | 1 | H | H |
| 574 | 5-Cl-1,2,4-Triazin-3-yl | S | 1 | H | H |
| 575 | 1,2,4-Triazin-5-yl | O | 1 | H | H |
| 576 | 1,2,4-Triazin-5-yl | S | 1 | H | H |
| 577 | 3-Cl-1,2,4-Triazin-5-yl | O | 1 | H | H |
| 578 | 3-Cl-1,2,4-Triazin-5-yl | S | 1 | H | H |
| 579 | 1,2,4-Triazin-6-yl | O | 1 | H | H |
| 580 | 1,2,4-Triazin-6-yl | S | 1 | H | H |
| 581 | 3-Cl-1,2,4-Triazin-6-yl | O | 1 | H | H |
| 582 | 3-Cl-1,2,4-Triazin-6-yl | S | 1 | H | H |
| 583 | 6-Cl-1,3,5-Triazin-2-yl | O | 1 | H | H |
| 584 | 6-Cl-1,3,5-Triazin-2-yl | S | 1 | H | H |
| 585 | 4,6-Di-Cl-1,3,5-triazin-2-yl | O | 1 | H | H |
| 586 | 4,6-Di-Cl-1,3,5-triazin-2-yl | S | 1 | H | H |
| 587 | 1,2,4-Benzotriazin-3-yl | O | 1 | H | H |
| 586 | 1,2,4-Benzotriazin-3-yl | S | 1 | H | H |
| 589 | 1,2,4,5-Tetrazin-3-yl | O | 1 | H | H |
| 590 | 1,2,4,5-Tetrazin-3-yl | S | 1 | H | H |
| 591 | 6-Cl-1,2,4,5-Tetrazin-3-yl | O | 1 | H | H |
| 592 | 6-Cl-1,2,4,5-Tetrazin-3-yl | S | 1 | H | H |
| 593 | <u>N</u>—(CO$_2$CH$_3$)-Pyrrolidin-3-yl | O | 1 | H | H |
| 594 | <u>N</u>—(CO$_2$CH$_3$)-Pyrrolidin-3-yl | S | 1 | H | H |

* For these values of X and Z, see under "Chemical Formulae" later.

TABLE II

Table II comprises 594 compounds of the general formula (I.4) with all the values of Z, X, q, A and B listed in Table I. That is, compounds numbers 1 to 594 of Table II are the same as those of Table I except that the pyrimidine ring is linked to the other two rings through its 4- and 6-positions in Table I and through its 2- and 4-positions in Table II.

TABLE III

Table III comprises 594 compounds of the general formula (I.5) with all the values of Z, X, q, A and B listed in Table I. That is, compounds numbers 1 to 594 of Table III are the same as those of Table I except that the pyrimidine ring is linked to the other two rings through its 4- and 6-positions in Table I and through its 2- and 4-positions in Table III.

TABLE IV

Table IV comprises 594 compounds of the general formula (I.6) with all the values of Z, X, q, A and B listed in Table I. That is, compounds numbers 1 to 594 of Table IV are the same as those of Table I except that the pyrimidine ring is linked to the benzene ring carrying the acrylate group by oxygen in Table I and sulphur in Table IV.

TABLE V

Table V comprises 594 compounds of the general formula (I.7) with all the values of Z, X, q, A and B listed in Table I. That is, compound numbers 1 to 594 of Table V are the same as those of Table I except that (a) the pyrimidine ring is linked to the benzene ring carrying the acrylate group by oxygen in Table I and sulphur in Table V; and (b) the pyrimidine ring is linked to the other two rings through its 4- and 6-positions in Table I and through its 2- and 4-positions in Table V.

TABLE VI

Table VI comprises 594 compounds of the general formula (I.8) with all the values of Z, X, q, A and B listed in Table I. That is, compounds numbers 1 to 594 of Table VI are the same as those of Table I except that (a) the pyrimidine ring is linked to the benzene ring carrying the acrylate group by oxygen in Table I and sulphur in Table VI; and (b) the pyrimidine ring is linked to the other two rings through its 4- and 6-positions in Table I and through its 2- and 4-positions in Table VI.

TABLE VII

SELECTED PROTON NHR DATA

Table VII shows selected proton NMR data for certain compounds described in Table I. Chemical shifts are measured in ppm from tetra-methylsilane. Deuterochloroform was used as solvent and the operating frequency of the NMR spectrometer was 270 MHz throughout.
The following abbreviations are used:
- br = broad
- dd = double doublet
- ppm = parts per million
- m = multiplet
- s = singlet
- d = doublet
- t = triplet
- q = quartet

| Compound No | NMR DATA |
|---|---|
| 96 | 3.05(2H, t), 3.55(3H, s), 3.65(3H, s), 4.55(2H, t), 6.00(1H, s), 7.15–7.40((9H, m), 7.42(1H, s), 8.40(1H, s) ppm. |
| 218 | 3.58(3H, s), 3.71(3H, s), 6.74(1H, s), 7.12–7.43(5H, m), 7.44(1H, s), 7.61–7.79(2H, m), 8.56(1H, s), 8.61–8.68(1H, m) ppm. |
| 222 | 3.59(3H, s), 3.72(3H, s), 5.50(2H, s), 6.20(1H, s), 7.15–7.40(6H, m), 7.46(1H, s), 7.70(1H, t), 8.60(1H, d), 8.42(1H, s) ppm. |
| 229 | 3.58(3H, s), 3.70(3H, s), 5.40(2H, s), 6.10(1H, s), 7.15(1H, d), 7.30(4H, m), 7.44(1H, s), 7.75(1H, d), 8.42(1H, s), 8.58(1H, d), 8.69(1H, s) ppm. |
| 236 | 3.59(3H, s), 3.75(3H, s), 5.42(2H, s), 6.18(1H, s), 7.18(1H, d), 7.25–7.40(5H, m), 7.45(1H, s), 8.42(1H, s), 8.60(2H, d) ppm. |
| 239 | 3.57(3H, s), 3.72(3H, s), 7.13–7.50(5H, m), 7.47(1H, s), 7.60(1H, s), 8.64(2H, d), 8.68(1H, s) ppm. |
| 250 | 3.60(3H, s), 3.75(3H, s), 5.50(2H, s), 6.23(1H, s), 7.18(1H, d), 7.27–7.42(4H, m), 7.47(1H, s), 8.41(1H, s), 8.74(1H, d), 9.19(1H, s) ppm. |
| 271 | 3.59(3H, s), 3.75(3H, s), 5.75(2H, s), 6.20(1H, s), 7.15(1H, d), 7.28–7.40(3H, m), 7.46(1H, s), 7.50(1H, m), 7.65(1H, d), 8.42(1H, s), 9.15(1H, dd) ppm. |
| 320 | 3.58(3H, s), 3.70(3H, s), 5.35(2H, s), 6.05(1H, s), 6.35(1H, d), 6.45(1H, d), 7.15(1H, d), 7.20–7.40(4H, m), 7.44(1H, s), 8.45(1H, s) ppm. |
| 357 | 3.30(2H, t), 3.57(3H, s), 3.70(3H, s), 4.60(2H, t), 6.03(1H, s), 7.15(1H, d), 7.25–7.40(5H, m), 7.45(1H, s), 7.55(1H, m), 7.65(1H, d), 8.39(1H, s) ppm. |
| 358 | 3.35(2H, t), 3.58(3H, s), 3.72(3H, s), 4.63(2H, t), 6.03(1H, s), 7.15(1H, d), 7.25–7.42(5H, m), 7.45(1H, s), 7.54(1H, d), 7.95(1H, d), 8.39(1H, s) ppm. |
| 359 | 3.10(2H, t), 3.55(3H, s), 3.70(3H, s), 4.55(2H, t), 6.0(1H, s), 7.15(1H, d), 7.28–7.40(5H, m), 7.43(1H, s), 7.60(2H, d), 8.40(1H, s) ppm. |
| 360 | 2.05(2H, m), 2.75(2H, t), 3.55(2H, s), 3.72(3H, s), 4.32(2H, t), 6.05(1H, s), 7.20(4H, m), 7.30(5H, m), 7.44(1H, s), 8.40(1H, s) ppm. |
| 361 | 2.15(2H, m), 3.05(2H, t), 3.60(3H, s), 3.75(3H, s), 4.35(2H, t), 6.05(1H, s), 7.18(1H, d), 7.29–7.40(5H, m), 7.46(1H, s), 7.52(1H, m), 7.91(1H, d), 8.40(1H, s) ppm. |
| 363 | 3.25(2H, t), 3.55(3H, s), 3.70(3H, s), 4.55(2H, t), 6.05(1H, s), 7.17(1H, d), 7.26–7.50(6H, m), 7.45(1H, s), 7.65(1H, d), 8.40(1H, s) ppm. |
| 364 | 2.35(3H, s), 3.05(2H, t), 3.55(3H, s), 3.70(3H, s), 4.50(2H, t), 6.02(1H, s), 7.15(5H, m), 7.25–7.40(3H, m), 7.44(1H, s), 8.40(1H, s) ppm. |
| 365 | 3.05(2H, t), 3.55(3H, s), 3.70(3H, s), 3.80(3H, s), 4.50(2H, t), 6.00(1H, s), 6.85(2H, m), 7.12–7.40(6H, m), 7.43(1H, s), 8.40(1H, s) ppm. |
| 366 | 3.10(2H, t), 3.55(3H, s), 3.70(3H, s), 4.55(2H, t), 6.00(1H, s), 7.00–7.40(8H, m), 7.43(1H, s), 8.40(1H, s) ppm. |
| 368 | 3.20(2H, t), 3.55(3H, s), 3.70(3H, s), 4.55(2H, t), 6.00(1H, s), 7.20(2H, m), 7.23–7.40(6H, m), 7.44(1H, s), 8.40(1H, s) ppm. |
| 370 | 3.15(2H, t), 3.55(3H, s), 3.70(3H, s), 4.50(2H, t), 6.00(1H, s), 6.85(2H, t), 7.15(2H, m), 7.25–7.4(3H, m), 7.44(1H, s), 8.40(1H, s) ppm. |
| 371 | 3.55(3H,s), 3.68(3H, s), 6.20(1H, s), 6.65(1H, q), 7.15(1H, d), 7.30–7.40(6H, m), 7.42(1H, s), 7.50(2H, m), 8.36(1H, s) ppm. |
| 372 | 3.25(2H, t), 3.55(3H, s), 3.70(3H, s), 4.52(2H, t), 6.05(1H, s), 6.95(1H, m), 7.15(3H, m), 7.30(3H, m), 7.44(1H, s), 8.40(1H, s) ppm. |
| 373 | 3.40(2H, t), 3.60(3H, s), 3.73(3H, s), 4.55(2H, t), 6.05(1H, s), 7.15(2H, m), 7.25–7.40(5H, m), 7.45(1H, s), 8.40(1H, s) ppm. |
| 374 | 3.50(3H, s), 3.65(3H, s), 5.38(2H, s), 5.95(1H, s), 6.85(1H, t), 7.06(1H, d), 7.18–7.30(4H, m), 7.35(1H, s), 8.40(1H, s) ppm. |
| 376 | 3.55(3H, s), 3.70(3H, s), 5.02(2H, d), 6.10(1H, s), 6.40(1H, m), 6.70(1H, d), 7.15(1H, d), 7.20–7.40(8H, m), 7.45(1H, s), 8.45(1H, s) ppm. |
| 382 | 3.60(3H, s), 3.75(3H, s), 4.45(2H, m), 4.65(2H, m), 6.10(1H, s), 6.8–7.0(3H, m), 7.15(1H, d), 7.28–7.4(3H, m), 7.45(1H, s), 8.40(1H, s) ppm. |
| 384 | 2.10(2H, m), 2.88(2H, m), 3.60(3H, s), 3.75(3H, s), 4.35(2H, t), 6.05(1H, s), 7.15–7.45(8H, m), 7.45(1H, s), 8.42(1H, s) ppm. |
| 385 | 3.58(3H, s), 3.70(3H, s), 5.60(2H, s), 6.10(1H, s), 7.18(1H, d), 7.25–7.50(4H, m), 7.45(1H, s), 7.52–7.72(3H, m), 8.45(1H, s) ppm. |

TABLE VII-continued

SELECTED PROTON NHR DATA

| | |
|---|---|
| 386 | 3.58(3H, s), 3.70(3H, s), 5.52(2H, d), 6.05(1H, s), 7.05(1H, s), 7.18(1H, d), 7.20–7.40(5H, m), 7.45(1H, s), 8.50(1H, s) ppm. |
| 387 | 3.58(3H, s), 3.70(3H, s), 5.20(2H, s), 6.15(1H, s), 7.18(1H, d), 7.25–7.40(6H, m), 7.43(1H, s), 7.43(2H, m), 8.45(1H, s) ppm. |
| 388 | 3.58(3H, s), 3.72(3H, s), 5.48(2H, s), 6.05(1H, s), 7.15(1H, d), 7.20–7.40(3H, m), 7.45(1H, s), 8.45(1H, s) ppm. |
| 391 | 3.25(2H, t), 3.60(3H, s), 3.70(3H, s), 4.50(2H, t), 6.00(1H, s), 7.10–7.50(9H, m), 7.43(1H, s), 8.40(1H, s) ppm. |
| 392 | 3.58(3H, s), 3.72(3H, s), 5.85–6.05(1H, br), 7.11–7.15(1H, d), 7.23–7.60(7H, m), 7.42(1H, s), 8.15(1H, s), 8.48(1H, s), 9.80–9.95(1H, br) ppm. |
| 393 | 3.40(2H, t), 3.60(3H, s), 3.75(3H, s), 4.55(2H, t), 6.00(1H, s), 7.15(1H, d), 7.25–7.40(4H, m), 7.45(1H, s), 7.50–7.70(3H, m), 8.40(1H, s) ppm. |
| 394 | 3.55(3H, s), 3.70(3H, s), 5.55(2H, s), 6.05(1H, s), 7.00(1H, m), 7.15(2H, m), 7.25–7.40(4H, m), 7.43(1H, s), 8.45(1H, s) ppm. |
| 395 | 3.60(3H, s), 3.75(3H, s), 5.10(2H, d), 6.13(1H, s), 6.60(1H, m), 7.04–7.20(2H, m), 7.25–7.40(4H, m), 7.46(1H, s), 7.52–7.70(3H, m), 8.45(1H, s) ppm. |
| 396 | 3.60(3H, s), 3.73(3H, s), 4.40(2H, t), 4.75(2H, t), 6.10(1H, s), 7.00(2H, m), 7.18(1H, d), 7.25–7.40(3H, m), 7.45(1H, s), 7.50–7.60(2H, m), 8.43(1H, s) ppm. |
| 397 | 3.60(3H, s), 3.73(3H, s), 4.60(2H, t), 4.72(2H, t), 6.10(1H, s), 7.05–7.2(2H, m), 7.25–7.40(5H, m), 7.46(1H, s), 8.40(1H, s) ppm. |
| 399 | 2.72(3H, s), 3.59(3H, s), 3.74(3H, s), 6.93(1H, t), 7.01(1H, d), 7.06(1H, d), 7.20–7.52(5H, m), 7.47(1H, s), 7.65(1H, m), 8.76(1H, s), 12.28(1H, br s) ppm. |
| 401 | 1.44(3H, t), 3.58(3H, s), 3.73(3H, s), 4.10(2H, q), 6.16(1H, s), 6.87–7.41(8H, m), 7.45(1H, s), 7.81(1H, d), 8.40(1H, s) ppm. |
| 402 | 0.98(3H, t), 1.41–1.55(2H, m), 1.75–1.85(2H, m), 3.58(3H, s), 3.72(3H, s), 4.02(2H, t), 6.17(1H, s), 6.89–7.41(8H, m), 7.46(1H, s), 7.79(1H, d), 8.39(1H, s) ppm. |
| 403 | 2.52(3H, s), 3.57(3H, s), 3.70(3H, s), 6.82(1H, s), 7.20–7.50(7H, m), 7.48(1H, s), 7.75(2H, m), 8.49(1H, s) ppm. |
| 405 | 3.58(3H, s), 3.70(3H, s), 5.36(2H, s), 6.08(1H, s), 7.05(2H, t), 7.15(1H, d), 7.24–7.43(5H, m), 7.43(1H, s), 8.44(1H, s) ppm. |
| 593 | 2.97(3H, s), 3.58(3H, s), 3.64(1H, m), 3.75(3H, s), 3.82(1H, m), 4.14(1H, t), 4.55(1H, t), 4.72(1H, m), 5.70(1H, s), 7.15(1H, d), 7.21–7.38(3H, m), 7.45(1H, s), 8.24(1H, s) ppm. |

TABLE VIII

MELTING POINTS AND OLEFINIC PROTON NMR DATA

Table VIII shows melting points and olefinic proton NMR data for certain compounds described in Tables I to VI. Melting points are in ° C. and the column headed 'olefinic' shows the chemical shift of the singlet from the olefinic proton on the β-methoxypropenoate group, measured in ppm from tetramethylsilane. Deuterochloroform was used as the solvent throughout.

| Table No | Compound No | Olefinic (ppm) | Melting Point (° C.) |
|---|---|---|---|
| I | 1 | 7.40 | 75–8 |
| I | 2 | 7.42 | 108–110 |
| I | 3 | 7.44 | 126–8 |
| I | 4 | 7.45 | Foam |
| I | 9* | 7.40 or 7.44 | Oil |
| I | 23 | 7.45 | Gum |
| I | 96 | 7.42 | Oil |
| I | 133 | 7.45 | 96–8 |
| I | 134 | 7.45 | 110–2 |
| I | 180 | 7.46 | Gum |
| II | 180 | 7.43 | 129–131 |
| III | 180 | 7.43 | 98–100 |
| I | 218 | 7.44 | Gum |
| I | 220 | 7.47 | Foam |
| I | 222 | 7.46 | Gum |
| I | 229 | 7.44 | Gum |
| I | 236 | 7.45 | Gum |
| I | 239 | 7.47 | 79–81 |
| I | 250 | 7.47 | Gum |
| I | 271 | 7.46 | Gum |
| I | 320 | 7.44 | Gum |
| I | 354 | 7.47 | Foam |
| I | 355 | 7.42 | 57 |
| I | 356 | 7.49 | 67 |
| I | 357 | 7.45 | Gum |
| I | 358 | 7.45 | Gum |
| I | 359 | 7.43 | Oil |
| I | 360 | 7.44 | Gum |
| I | 361 | 7.46 | Gum |
| I | 362 | 7.47 | Foam |
| I | 363 | 7.45 | Gum |
| I | 364 | 7.44 | Gum |
| I | 365 | 7.43 | Gum |
| I | 366 | 7.43 | Gum |
| I | 367 | 7.48 | 104–8 |
| I | 368 | 7.44 | Gum |
| I | 369 | 7.45 | Oil |
| I | 370 | 7.44 | Gum |
| I | 371 | 7.42 | Gum |
| I | 372 | 7.44 | Gum |
| I | 373 | 7.45 | Gum |
| I | 374 | 7.35 | Gum |
| I | 375 | 7.46 | 104–6 |
| I | 376 | 7.45 | Gum |
| I | 377 | 7.46 | Foam |
| II | 378 | 7.44 | 118–120 |
| I | 379 | 7.45 | 81–5 |
| I | 380 | 7.45 | 60–3 |
| I | 381 | 7.45 | 151–2 |
| I | 382 | 7.45 | Gum |
| I | 383 | 7.47 | 101–2 |
| I | 384 | 7.45 | Gum |
| I | 385 | 7.45 | Gum |
| I | 386 | 7.45 | Gum |
| I | 387 | 7.43 | Gum |
| I | 388 | 7.45 | Gum |
| I | 389 | 7.45 | Gum |
| I | 390 | 7.44 | 131–2 |
| I | 391 | 7.43 | Gum |
| I | 392 | 7.42 | Gum |
| I | 393 | 7.45 | Gum |
| I | 394 | 7.43 | Gum |
| I | 395 | 7.46 | Gum |
| I | 396 | 7.45 | Gum |
| I | 397 | 7.46 | Gum |
| I | 398 | 7.46 | Foam |
| I | 399 | 7.47 | Gum |
| I | 400 | 7.46 | 160–1 |
| I | 401 | 7.45 | Foam |
| I | 402 | 7.46 | Gum |
| I | 403 | 7.48 | Low mp solid |
| I | 404 | 7.48 | 138–40 |
| I | 405 | 7.43 | Gum |
| I | 406 | 7.48 | 80 |
| I | 407 | 7.47 | 65–70 |

TABLE VIII-continued

MELTING POINTS AND OLEFINIC PROTON NMR DATA
Table VIII shows melting points and olefinic proton NMR data for certain compounds described in Tables I to VI. Melting points are in ° C. and the column headed 'olefinic' shows the chemical shift of the singlet from the olefinic proton on the β-methoxypropenoate group, measured in ppm from tetramethylsilane. Deuterochloroform was used as the solvent throughout.

| Table No | Compound No | Olefinic (ppm) | Melting Point (° C.) |
|---|---|---|---|
| I | 415 | 7.48 | 106–106.5 |
| I | 420 | 7.46 | 119.5–120.5 |
| I | 530 | 7.44 | Gum |
| I | 593 | 7.45 | Gum |

*This sample contains 50% of (E)-methyl 2-(2-(4-n-butylpyrimidin-6-yloxy)phenyl)-3-methoxypropenoate.

The compounds of the invention of formula (I) [equivalent to (IA) when W is the group $CH_3O_2C.C=CH.OCH_3$ and $Z^1$ is Z; and equivalent to (IB) when W is the group $CH_3O_2C.C=CH.OCH_3$] can be prepared by the steps shown in Schemes I and II. In these Schemes, K, L, M, Z, X, q, A, E, T, $R^1$ and $R^4$ are as defined above; $Z^1$ is Z or a group which can be converted by standard procedures described in the chemical literature into Z; W is $CH_3O_2C.C=CH.OCH_3$ or a group that can be transformed into $CH_3O_2C.C=CHOCH_3$ using methods previously described such as in EP-A-0242081; U is a leaving group such as a halogen or $CH_3SO_2$—; V is hydrogen or a metal (such as sodium); R is $C_{1-4}$ alkyl or aryl, especially phenyl; and Y is a group which can be converted by standard procedures described in the chemical literature into the group $Z(X)_q$—. The reactions shown in Schemes I and II are performed either in a suitable solvent or without a solvent, and at a suitable temperature.

Thus compounds of formula (IA) (equivalent to compounds of the invention when W is $CH_3O_2C.C=CH.OCH_3$ and $Z^1$ is Z) can be prepared by treatment of pyrimidines of formula (IV) with phenols/thiophenols or phenolates/thiophenolates of formula (II) or by treatment of pyrimidines of formula (V) with substituted benzenes of formula (III) (Scheme I). In each case, the reaction is carried out in the presence of a base (such as potassium carbonate) if V is hydrogen.

Compounds of formula (IB) (equivalent to the compounds of the invention when V is $CH_3O_2C.C=CH.OCH_3$) can be prepared from pyrimidines of formula (VI) (Scheme II). The term Y in formulae (VI), (VII) and (VIII) represents a group which can be converted by standard procedures described in the chemical literature into the group $Z(X)_q$—; for example, Y may be a halogen (such as fluorine, chlorine or bromine) or —OH, —SH, —$NHR^4$, —$CO_2H$, —COCl, —$CHR^1OH$, —C(O)$R^1$, —$CHR^1$—U (where U is a leaving group such as a halogen), —$SO_2R^1$, —$SO_2OH$, —$SO_2Cl$, —$CHR^1P(O)(OR)_2$ or —$CHR^1P^+R_3$ (counter-ion)⁻. Compounds of formula (VI) in which W is $CH_3O_2C.C=CH.OCH_3$ and Y has the values listed in the preceding sentence are especially valuable intermediates for the preparation of the compounds of the invention.

Pyrimidines of formula (VI) can be prepared by treatment of phenols/thiophenols or phenolates/thiophenolates of formula (II) with pyrimidines of formula (VII) or by treatment of substituted benzenes of formula (III) with pyrimidines of formula (VIII) (Scheme II). In each case, the reaction is carried out in the presence of a base (such as potassium carbonate) if V is hydrogen.

Modifications to the group V may be made at any appropriate stage in the pathways shown in Schemes I and II. For example, if W is the group —$CH_2CO_2CH_3$ during the conversion of (VI) into (IB) (Scheme II), it may be converted at the last stages of the synthesis into the group $CH_3O_2C.CCH.OCH_3$.

The substitutents A, E and B (one of K, L, M having the value CB wherein B is as defined above) as well as any substituents on the aryl or heterocyclyl ring Z may also be modified at any appropriate reaction step. If, for example, A is a halogen such as chlorine, it may be removed at an appropriate stage of the synthesis (such as the last stage) to give the corresponding pyrimidine in which A is hydrogen. Or if, as a further example, E is $NO_2$ it may be converted via reduction and diazotisation into a halogen, cyano or hydroxyl group, and this may be carried out on intermediates such as (II) or (VI) or on the compounds of formula (IA) or (IB).

Modifications to the linking group X (such as reducing an olefinic bond or oxidising a sulphur atom) may also be made at any appropriate reaction step.

N-Oxides and N-alkyl salts can be made by N-oxidation or quaternisation, respectively, of appropriate intermediates or of the final compounds of the invention.

Pyrimidines of formulae (IV), (V), (VII) and (VIII) can be prepared by standard methods described in the literature. Compounds of formulae (II) and (III) can also be made by standard methods or, when W is $CH_3O_2C.C=CH.OCH_3$, can be made by methods described in EP-A-0242081 (T is oxygen) and EP-A-0178826 respectively.

In a further aspect the invention provides processes as herein described for preparing the compounds of formula (I). It also includes the compound, (E)-methyl 2-[2-(6-hydroxypyrimidin-4-yloxy)phenyl]-3-methoxy-propenoate.

The compounds are active fungicides and may be used to control one or more of the following pathogens : *Pyricularia oryzae* on rice; *Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants; *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines; Helminthosporium spp., Rhynchosporium spp., Septoria spp., Pyrenophora spp., *Pseudocercosporella herpotrichoides* and *Gaeumannomyces graminis* on cereals; *Cercospora arachidicola* and *Cercosporidium personata* on peanuts and other Cercospora species on other hosts, for example, sugar beet, bananas, soya beans and rice; *Botrytis cinerea* (grey mould) on tomatoes, strawberries, vegetables, vines and other hosts; Alternaria spp. on vegetables (e.g. cucumber), oil-seed rape, apples, tomatoes and other hosts; *Venturia inaequalis* (scab) on apples; *Plasmopara viticola* on vines; other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits; *Phytophthora infestans* on potatoes and tomatoes and other Phytophthora spp. on vegetables, strawberries, avocado, pepper, ornamentals, tobacco, cocoa and other hosts; *Thanatephorus cucumeris* on rice and other Rhizoctonia species on various hosts such as wheat and barley, vegetables, cotton and turf. Some of the compounds show a broad range of activities against fungi in vitro. They may also have activity against various post-harvest diseases of fruit (e.g. *Penicillium digitatum* and *italicum* and *Trichoderma virlde* on oranges, *Gloeosporium musarum* on bananas and *Botrytis cinerea* on grapes).

Further, some of the compounds may be active as seed dressings against pathogens including Fusarium spp., Septoria spp., Tilletia spp., (bunt, a seed-borne disease of wheat), Ustilago spp. and Helminthosporium spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants.are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or N,N-dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, etyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and tri-isopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2-(1H-1,2,4-triazol-1-ylmethyl) butyronitrile, (Z)-N-but-2-enyloxymethyl-2-chloro-2',6'-diethylacetanilide, 1-(2-cyano-2-methoxyiminoacetyl)-3-ethyl urea, 3-(2,4-dichlorophenyl)-2-(1H-1,2,4-triazol-1-yl) quinazolin-4(3H)-one, 4-bromo-2-cyano-N,N-dimethyl-6-trifluoromethylbenzimidazole-1-sulphonamide, 5-ethyl-5,8-dihydro-8-oxo(1,3)-dioxol-(4,5-g)quinoline-7-carboxylic acid, α-[N-(3-chloro-2,6-xylyl)-2-methoxyacetamido)-γ-butyrolactone, aldimorph, anilazine, benalaxyl, benomyl, biloxazol, binapacryl, bitertanol, blasticidin S, bromuconazole, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-benzyl-N-([methyl(methylthioethylideneamino-oxycarbonyl)amino]thio)-β-alaninate, etridiazole, fenapanil, fenarimol, fenfuram, fenpiclonil, fenpropidin, fenprpimorph, fentin acetate, fentin hydroxide, flutolanil, flutriafol, flusilazole, folpet, fosetyl-aluminium, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepanipyrim, mepronil, metalaxyl, methfuroxam, metsulfovax, myclobutanil, neoasozin, nickel dimethyldithiocarbamate, nitrothal-isopropyl, nuarimol, ofurace, organomercury compounds, oxadixyl, oxycarboxin, pefurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, SSF-109, streptomycin, sulphur, tebuconazole, techlofthalam, tecnazene, tetraconazole, thiabendazole, thicyofen, thiophanate-methyl, thiram, tolclofos-methyl, triacetate salt of 1,1'-iminodi(octamethylene)diguanidine, triadimefon, triadimenol, triazbutyl, tricyclazole, tridemorph, triforine, validamycin A, vinclozolin, zarilamid and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant grovth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-di-methyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxy-benzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxy-acetic acids (e.g. 2,4-D or MCPA), substituted benzoic acid (e.g. trilodobenzoic acid), substituted quaternary ammonium and phosphonium compounds (e.g. chloromequat, chlorpho-nium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following Examples illustrate the invention. Throughout the Examples, the term 'ether' refers to diethyl ether, magnesium sulphate was used to dry solutions, and solutions were concentrated under reduced pressure. Reactions involving water-sensitive intermediates were performed under an atmosphere of nitrogen and solvents were dried before use, where appropriate. Unless otherwise stated, chromatography was performed on a column of silica gel as the stationary phase. Where shown, infrared and NHR data are selective; no attempt is made to list every absorption in all cases. $^1$H NMR spectra were recorded using $CDCl_3$ solutions unless otherwise stated. (E)-Methyl 2-(2-hydroxyphenyl)-3-methoxypropenoate, used as an intermediate in several of the following Examples, was prepared as described in Example 3 of EP-A-0242081. Similarly, (E)-methyl 2-[2-(6-chloropyrimidin-4-yloxy)phenyl]-3-methoxypropenoate was prepared as described in Example 3 of EP-A-0382375. The following abbreviations are used throughout:

| | | | |
|---|---|---|---|
| DME = | dimethoxyethane | s = | singlet |
| THF = | tetrahydrofuran | d = | doublet |
| DMF = | N,N-dimethylformamide | dd = | doublet of doublets |
| DMSO = | dimethyl sulphoxide | t = | triplet |
| NMR = | nuclear magnetic resonance | m = | multiplet |
| IR = | infrared | br = | broad |
| mp = | melting point | ppm = | parts per million |
| GC = | gas chromatography | | |
| TLC = | thin layer chromatography | | |
| HPLC = | high performance liquid chromatography | | |

EXAMPLE 1

This Example illustrates the preparation of (E)-methyl 2-[2-(6-(2-cyanoanilino)pyrimidin-4-yloxy)phenyl]-3-methoxypropenoate (Compound No. 377 of Table I).

(E)-Nethyl 2-[2-(6-chloropyrimidin-4-yloxy)phenyl]-3-methoxypropenoate (1.0 g), was treated with sodium methanethiolate (1.09 g) at room temperature in chloroform (15 ml) and water (10 ml) in the presence of a catalytic amount of tetrabutylammonium bromide. After stirring overnight, the chloroform layer was separated and the remaining aqueous layer was further extracted with chloroform. The combined chloroform layers were washed with water, dried and concentrated to give an orange oil. Chromatography using a mixture of ether and hexane (2:1) gave (E)-methyl 2-(2-(6-methylthiopyrimidin-4-yloxy)phenyl]-3-methoxypropenoate (0.92 g, 89% yield) as a pale yellow oil; 1H NMR: δ 2.52 (3H, s), 3.59 (3H, s), 3.73 (3H, s), 6.55 (1H, s), 7.17 (1H, d), 7.20–7.55 (3H, m), 7.45 (1H, s), 8.57 (1H, s) ppm.

The product (0.2 g) was stirred with 3-chloroperbenzoic acid (0.38 g of a 55% damp paste) in chloroform (25 ml) at room temperature for 16 hours. The reaction mixture was poured into a saturated solution of sodium metabisulphite (50 ml), the organic extract was separated and the aqueous layer was extracted with more chloroform. The combined chloroform solutions were washed with a saturated solution of sodium bicarbonate, then dried and concentrated to give (E)-methyl 2-[2-(6-methanesulphonylpyrimidin-4-yloxy)phenyl]-3-methoxypropenoate (0.26 g) as a colourless oil; $^1$H NMR: δ 3.18 (3H, s), 3.55 (3H, s), 3.68 (3H, s), 7.1–7.4 (5H, m), 7.40 (1H, s), 8.81 (1H, s) ppm.

2-Cyanoformanilide (0.2 g) was added to a suspension of sodium hydride (0.035 g) in DMF (15 ml). After 40 minutes the reaction mixture was cooled to 0° C. and (E)-methyl 2-[2-(6-methanesulphonylpyrimidin-4-yloxy)phenyl]-3-methoxypropenoate (0.5 g) in DMF (5 ml) was added dropwise. The reaction mixture was stirred for 16 hours before being poured into water and extracted with ethyl acetate. The combined extracts were washed with brine and concentrated to give an orange oil, which was purified by chromatography using a mixture of ethyl acetate and hexane (1:1) as the eluent, to give the title compound (0.5 g, 95% yield) as a foam; 1H NMR: δ 3.61 (3H, s), 3.76 (3H, s), 6.13 (1H, s), 7.1–7.45 (6H, m), 7.46 (1H, s), 7.5–7.7 (2H, m), 8.13 (1H, d), 8.45 (1H, s) ppm.

EXAMPLE 2

This Example illustrates the preparation of (E)-methyl 2-[2-(6-(2-cyano-N-methylanilino)-pyrimidin-4-yloxy)phenyl]-3-methoxypropenoate (Compound No. 354 of Table I).

A solution of (E)-methyl 2-[2-(6-(2-cyanoanilino)pyrimidin-4-yloxy)-phenyl]-3-methoxypropenoate (0.5 g, as prepared in Example 1) in DMF (5 ml) was added to a suspension of sodium hydride (0.05 g) in DMF (10 ml) at 0° C. After 2 hours methyl iodide (0.12 ml) was added and the reaction mixture was stirred for a further 3 hours. The reaction mixture was then poured into water and extracted with a mixture of ethyl acetate and ether (1:1). The combined extracts were washed with brine, dried and concentrated to give an oil. Chromatography using ethyl acetate as the eluent gave the title compound (0.123 g, 24% yield) as a cream coloured foam; $^1$NMR: δ 3.46 (3H, s), 3.60 (3H, s), 3.72 (3H, s), 5.74 (1H, s), 7.1–7.8 (8H, m), 7.47(1H, s), 8.36 (1H, s) ppm.

EXAMPLE 3

This Example illustrates the preparation of (E)-methyl 2-[2-{6-(pyrid-2-ylamino)pyrimidin-4-yloxy}phenyl]-3-methoxypropenoate (Compound No.220 of Table I).

2-Formylaminopyridine (0.167 g) vas added to a suspension of sodium hydride (0.035 g) in DMF (10 ml). After 40 minutes the reaction mixture was cooled to 0° C. and then (E)-methyl 2-[2-(6-methanesulphonylpyrimidin-4-yloxy)phenyl]-3-methoxypropenoate (0.5 g, prepared as in Example 1) in DMF (5 ml) was added dropwise. The reaction mixture was stirred for 16 hours before being poured into water and extracted with ethyl acetate. The combined extracts were washed with brine, and concentrated to give a pale oil, which was chromatographed using ether as the eluent to give the title compound (0.109 g, 21% yield) as a foam; $^1$H NMR: δ 3.58 (3H, s), 3.71 (3H, s), 6.9–7.7 (7H, m), 7.47 (1H, s), 8.27 (2H, m), 8.45 (1H, s), 8.66 (1H, s) ppm; mass spectrum M$^+$ 378.

EXAMPLE 4

This Example illustrates the preparation of (E)-methyl 2-[2-(6-anilinopyrimidin-4-yloxy)phenyl]-3-methoxypropenoate (Compound No.4 of Table I).

A solution of formanilide (0.21 g) in DMF (5 ml) was added dropvise to a suspension of sodium hydride (0.1 g) in DMF (10 ml). After 2 hours the reaction mixture was cooled to 0° C. and (E)-methyl 2-[2-(6-methanesulphonylpyrimidin-4-yloxy)phenyl]-3-methoxypropenoate (0.63 g) in DMF (5 ml) was added dropvise. The reaction mixture was stirred for 16 hours before being poured into water and extracted with ether. The combined extracts were washed with brine, dried and concentrated to give an oil. HPLC using ether as the eluent gave the title compound (0.13 g, 20% yield) as an off-white foam; $^1$H NMR: δ 3.58 (3H, s), 3.73 (3H, s), 6.13 (1H, s), 6.80 (1H, br s), 7.1–7.4 (9H, m), 7.45 (1H, s), 8.35 (1H, s) ppm; IR maxima (film): 1707, 1630 cm$^{-1}$; mass spectrum M 377.

EXAMPLE 5

This Example illustrates the preparation of (E)-methyl 2-[2-(6-di-benzoylaminopyrimidin-4-yloxy)phenyl]-3-methoxypropenoate (Compound No.398 of Table I).

Sodium azide (0.25 g) was added to a solution of (E)-methyl 2-[2-(6-chloropyrimidin-4-yloxy)phenyl]-3-methoxypropenoate (1.0 g) in DMF (30 ml). The reaction mixture was stirred for 2 hours at room temperature, then for 6 hours at 50° C. After cooling, the reaction mixture was poured into water and extracted with ether (3×100 ml). The combined extracts were washed with brine, dried and concentrated to give (E)-methyl 2-[2-(6-azidopyrimidin-4-yloxy)phenyl]-3-methoxypropenoate (1.02 g, 99%) as an oil; $^1$H NHR: δ 3.51 (3H, s), 3.65 (3H, s), 6.12 (1H, s), 7.0–7.35 (4H, m), 7.37 (1H, s), mass 8.47 (1H, s) ppm; IR maxima (film): 2135, 1711, 1635 cm$^{-1}$.

A solution of (E)-methyl 2-[2-(6-azidopyrimidin-4-yloxy)-3-methoxypropenoate (1.0 g) in methanol and Lindlar catalyst (0.2 g) was stirred under a blanket of hydrogen gas at 1 atmosphere of pressure. After 2 hours the solution was filtered and concentrated to give an oil which crystallized on trituration with hexane to give (E)-methyl 2-[2-(6-aminopyrimidin-4-yloxy)-phenyl]-3-methoxypropenoate (0.82 g, 90% yield) as a white solid, m.p. 158–160° C.; $^1$H NMR: δ 3.60 (3H, s), 3.75 (3H, s), 4.96 (1H, br.s), 5.73 (1H, s), 7.1–7.4 (4H, m), 7.45 (1H, s), 8.25 (1H, s) ppm; IR maxima (mull): 3346, 3200, 1706, 1637 cm$^{-1}$.

Benzoyl chloride (0.09 ml) was added to a stirred solution of (E)-methyl 2-[2-(6-aminopyrimidin-4-yloxy)phenyl]-3-methoxypropenoate (0.2 g) and triethylamine (0.12 ml) in ether (30 ml) at 0° C. The reaction mixture was stirred for 16 hours and then poured into water and extracted with ether. The combined ether extracts were washed successively with brine and saturated sodium bicarbonate solution and then dried, concentrated and chromatographed using a mixture of ethyl acetate and hexane (1:3) as the eluent, to give the title compound (0.23 g, 68% yield) as a clear foam; $^1$H NMR: δ 3.60 (3H, s), 3.68 (3H, s), 6.77 (1H, s), 7.0–7.45 (8H, m), 7.46 (1H, s), 7.5–7.6 (2H, m), 7.7–7.8 (4H, m), 8.53 (1H, s) ppm; IR maxima (mull): 1705, 1632 cm$^{-1}$.

EXAMPLE 6

This Example illustrates the preparation of (E)-methyl 2-[2-(6-chloro-2-phenylpyrimidin-4-yloxy)phenyl]-3-methoxypropenoate (Compound No.378 of Table II).

A stirred solution containing (E)-methyl 2-(2-hydroxyphenyl)-3-methoxypropenoate (208 mg) and 4,6-dichloro-2-phenylpyrimidine (225 mg, prepared according to the method of D. B. Harden, H. J. Mokrose and L. Strekowski, *J. Org. Chem*, 1988, 53, 4137–4140) in DMF (5 ml) was cooled to 0° C. Potassium carbonate (138 mg) was then added and stirring was continued at 0° C. under an atmosphere of nitrogen. After 3 hours, the temperature was allowed to rise to room temperature and stirring was continued overnight. The reaction mixture was diluted with water and then acidified with dilute hydrochloric acid. The resulting mixture was extracted with ether (×3) and the combined ether extracts were washed successively with dilute aqueous sodium hydroxide solution (×2) and water (×3) and then dried. Evaporation of the solvent gave an oil (0.31 g), which solidified on standing. Chromatography (eluent ether-hexane, 1:2) afforded the title compound (0.12 g, 30%) as an off-white solid; m.p. 118–120° C.; 1H NMR: δ 3.54 (3H, s), 3.67 (3H, s), 6.65 (1H, s), 7.22–7.50 (7H, m), 7.44 (1H, s), 8.28–8.33 (2H, m) ppm; IR maxima: 1708, 1631 cm$^{-1}$.

EXAMPLE 7

This Example illustrates the preparation of (E)-methyl 2-[2-phenyl-pyrimidin-4-yloxy)phenyl]-3-methoxypropenoate (Compound No.180 of Table II).

To a stirred solution of (E)-methyl 2-[2-(6-chloro-2-phenylpyrimidin-4-yloxy)phenyl]-3-methoxypropenoate (280 mg, prepared according to Example 6) in THF (7.5 ml) at room temperature was added 10% palladium on carbon catalyst (30 mg) and potassium carbonate (150 mg). A solution of sodium hypophosphite (200 mg) in water (3.7 ml) was added dropwise over a period of 10 minutes. There was effervesence and the temperature of the reaction mixture rose to 25° C. Further amounts of palladium catalyst were added after 1.75 hours and 2.25 hours (30 mg and 80 mg, respectively). After stirring for a further day, the reaction mixture was filtered. The filter was washed through with ethyl acetate and water and the combined aqueous phases were extracted with ethyl acetate (×2). The combined organic filtrates and washings were washed with water (×3) and dried. Evaporation of the solvent gave the title compound as an oil (230 mg) which solidified on cooling; m.p. 129–131° C.; $^1$H NMR: δ 3.51 (3H, s), 3.65 (3H, s), 6.65–6.68 (1H, d), 7.24–7.46 (7H, m), 7.43 (1H, s), 8.28–8.33 (2H, m), 8.58–8.60 (1H, d) ppm; IR maxima: 1703, 1630 cm$^{-1}$.

EXAMPLE 8

This Example illustrates the preparation of (E)-methyl 2-(2-(6-phenylpyrimidin-4-yloxy)phenyl]-3-methoxypropenoate (Compound No.180 of Table I).

To 2-mercapto-6-hydroxy-4-phenylpyrimidine (10 g) in '880' ammonia solution (100 ml) was carefully added Raney nickel (32.5 g, 50% slurry) portionvise. Immediate effervescence took place. The mixture was heated to reflux for 4 hours, filtered and concentrated under reduced pressure. The initial residue was azeotroped with toluene (×2) to remove final traces of water. The pale blue residue was dissolved in hot ethanol and filtered and then the filtrate was treated with charcoal. The resulting green solution was evaporated under reduced pressure to afford crude 4-hydroxy-6-phenylpyrimidine (4.65 g) as a green solid (m.p.>300° C.) which was used in the next stage without further purification.

Crude 4-hydroxy-6-phenylpyrimidine (3.65 g) was heated to reflux with phosphoryl chloride (40 ml) for 90 minutes. The reaction mixture was cooled and then concentrated under reduced pressure to afford a brown solid. The brown solid was partitioned between water and ether and the combined ether extracts washed with brine, dried and evaporated to give 4-chloro-6-phenylpyrimidine (2.18 g, 93.5% pure by GC analysis) as a yellow solid which was used directly in the next stage.

To a suspension of sodium methanethiolate (0.88 g) in dry DMF (15 ml) at 0° C. was added dropwise over 20 minutes a solution of 4-chloro-6-phenylpyrimidine (2.18 g) in dry DMF (25 ml). Ater stirring for a further 15 minutes, the temperature was allowed to rise to room temperature. After 2 hours the reaction mixture was poured into water and extracted with ether (×3). The combined ether extracts were washed with water (×2), dried, filtered and evaporated to give 4-methylthio-6-phenylpyrimidine (2.16 g, 87% pure by GC analysis) as a yellow liquid which was used directly in the next stage.

To a solution of 4-methylthio-6-phenylpyrimidine (2.16 g) in glacial acetic acid (15 ml) at 15° C. was added a solution of potassium permanganate (2.15 g) in water (50 ml). The reaction mixture was stirred at room temperature for 2 hours and then left to stand overnight. Gaseous sulphur dioxide was then passed through the reaction mixture at ca. 10° C. until decolourisation had taken place. The resulting white suspension was poured into water and extracted with chloroform (×3). The combined organic extracts were washed successively with a saturated solution of sodium hydrogen carbonate (×2) and water (×2) and then dried, filtered and evaporated to give a white solid (2.41 g). Recrystallisation from dichloromethane/petrol afforded 4-methanesulphonyl-6-phenylpyrimidine (1.57 g) m.p.109–111° C.

To (E)-methyl 2-(2-hydroxyphenyl)-3-methoxypropenoate (218 mg) and potassium carbonate (138 mg) in dry DMF (5 ml) at 0° C. was added dropwise over 10 minutes a solution of 4-methanesulphonyl-6-phenylpyrimidine (234 mg). After stirring for 15 minutes the temperature was allowed to reach room temperature. Ater 5¼ hours, more (E)-methyl 2-(2-hydroxyphenyl)-3-methoxypropenoate (45 mg) was added and stirring was continued for 45 minutes. The reaction mixture was left to stand overnight at room temperature and then poured into water and acidified with dilute hydrochloric acid. The resulting mixture was extracted with ether (×3) and the combined ether extracts were washed with dilute aqueous sodium hydroxide solution (×3) and water (×3). The organic phase was dried, filtered and evaporated to give an orange gum (0.37 g) which was chromatographed (eluent ether-hexane, 2:1) to afford the title compound (0.17 g) as a gum; $^1$H NMR: δ 3.57 (3H, s), 3.72 (3H, s), 7.14 (1H, s), 7.23–7.53 (7H, m), 7.46 (1H, s), 8.00–8.05 (2H, m), 8.85(1H, s) ppm; IR maxima: 1702, 1638 cm$^{-1}$.

EXAMPLE 9

This Example illustrates the preparation of (E)-methyl 2-[2-(4-phenylpyrimidin-2-yloxy)phenyl]-3-methoxypropenoate (Compound No.180 of Table III).

To a stirred suspension of sodium methanethiolate (0.35 g) in DMF (5 ml) at 0° C. was added dropvise a solution of 2-chloro-4-phenylpyrimidine (0.86 g, prepared from 2-chloropyrimidine according to the method of D B Harden et al., *J. Org. Chem.*, 1988, 53, 4137) in DMF (5 ml). Stirring was continued at 0° C. for 15 minutes and then the temperature was allowed to rise to room temperature. After a further 2 hours, the reaction mixture was diluted with water and then extracted with ether (×3). The combined ether extracts were washed with water, dried, filtered and evaporated to give 2-methylthio-4-phenylpyrimidine (0.76 g) as a brown solid which was used directly in the next stage.

To a solution of 2-methylthio-4-phenylpyrimidine (0.76 g) in dichloromethane (15 ml) at 0° C. was added portionvise over 15 minutes meta-chloroperbenzoic acid (1.65 g). The resulting white emulsion was warmed to room temperature and stirred for a further 3½ hours. The reaction mixture was evaporated to give a white solid. The solid was redissolved in dichloromethane and washed with saturated aqueous sodium bicarbonate solution (×2), and then with water (×2). The resulting solution was dried, filtered and evaporated to give crude 2-methanesulphonyl-4-phenylpyrimidine (0.84 g) as a yellowish solid which was used in the next stage without further purification.

To (E)-methyl 2-(2-hydroxyphenyl)-3-methoxypropenoate (0.75 g) and potassium carbonate (0.50 g) in dry DMF (5 ml) was added dropwise over 10 minutes a solution of 2-methanesulphonyl-4-phenylpyrimidine (0.84 g) in DMF (5 ml). After 15 minutes at 0° C., the temperature was allowed to attain room temperature. After standing over the weekend at room temperature, the reaction mixture was poured into water, acidified with dilute hydrochloric acid and then extracted with ether (×3). The combined organic extracts were washed with dilute aqueous sodium hydroxide (×3) and then with water (×3) and then dried, filtered and evaporated to afford a red gum (0.75 g). Repeated chromatography (eluents ether-hexane, 1:1 and then ether) gave the title compound as an off-white foam (0.03 g) which crystallised on trituration with petrol; m.p. 98–100° C.; $^1$H NMR: δ 3.52 (3H, s), 3.67 (3H, s), 7.25–7.50 (8H, m), 7.43 (1H, s), 8.01–8.05 (2H, m), 8.53–8.55 (1H, d) ppm; IR maxima: 1708, 1633 cm$^{-1}$; mass spectrum m/e 362 (M$^+$).

EXAMPLE 10

This Example illustrates the preparation of (E)-methyl 2-[2-(6-phenylthiopyrimidin-4-yloxy)phenyl]-3-methoxypropenoate (Compound No.1 of Table I).

To (E)-methyl 2-[2-(6-chloropyrimidin-4-yloxy)phenyl]-3-methoxypropenoate (0.96 g) and potassium carbonate (0.43 g) in dry DMF (10 ml) at room temperature was added a solution of thiophenol (0.35 g) in dry DMF (2 ml). After stirring for 2¼ hours, the reaction mixture vas.poured into water and then extracted with ether (×3). The combined ether extracts were washed with dilute aqueous sodium hydroxide and water (×3) and then dried, filtered and evaporated to give a yellow gum (1.33 g). Trituration with ether afforded the title compound as a white solid (0.91 g); m.p. 75–8° C.; $^1$H NMR: δ 3.55 (3H, s), 3.70 (3H, s), 6.24 (1H, s), 7.07–7.1 (1H, d), 7.20–7.36 (3H, m), 7.45–7.51 (3H, m), 7.40 (1H, s), 7.56–7.63 (2H, m), 8.50 (1H, s) ppm; IR maxima: 1707, 1626 cm$^{-1}$.

EXAMPLE 11

This Example illustrates the preparation of (E)-methyl 2-[2-(6-phenylsulphinylpyrimidin-4-yloxy)phenyl]-3-methoxypropenoate and (E)-methyl 2-[2-(6-phenylsulphonylpyrimidin-4-yloxy)phenyl]-3-methoxypropenoate (Compounds Nos. 2 and 3 respectively of Table I).

To a stirred solution of (E)-methyl 2-[2-(6-phenylthiopyrimidin-4-yloxy)phenyl]-3-methoxypropenoate (315 mg, prepared as in Example 10) in dichloromethane (5 ml) at 10° C. was added dropvise a solution of meta-chloroperbenzoic acid (0.58 g) in dichloromethane (10 ml). The temperature was allowed to rise to room temperature and stirring was continued overnight. The reaction mixture was evaporated to dryness and the white solid residue was redissolved in ethyl acetate. The solution was washed with dilute aqueous sodium hydroxide solution (×3) and water (×3), and then dried, filtered and evaporated to give a yellow gum (0.16 g). Chromatography (eluent ether-hexane, 4:1) afforded the sulphone title compound as a white solid (175 mg); m.p. 126–8° C.; $^1$H NMR: δ 3.58 (3H, s), 3.70 (3H, s), 7.14–7.18 (1H, d), 7.31–7.45 (3H, m), 7.44(1H, s), 7.55–7.62 (3H, m), 7.67–7.72 (1H, m), 8.05–8.09 (2H, m), 8.77 (1H, s) ppm; IR maxima: 1708, 1634, 1360, 1160 cm$^{-1}$; and the sulphoxide title compound (60 mg) as a colourless gum which crystallised on trituration with ether; m.p. 108–110° C.; $^1$H NMR: δ 3.53 (3H, s), 3.63 (3H, s), 7.14–7.18 (1H, d), 7.29–7.43 (3H, m), 7.42 (1H, s), 7.47–7.52 (3H, m), 7.55 (1H, s), 7.80–7.84 (2H, m), 8.65 (1H, s) ppm; IR maxima: 1708, 1633, 1050 cm$^{-1}$.

EXAMPLE 12

This Example illustrates the preparation of (E)-methyl 2-[2-(6-benzyloxypyrimidin-4-yloxy)phenyl]-3-methoxypropenoate (Compound No.23 of Table I).

To a stirred solution of (E)-methyl 2-[2-(6-methanesulphonylpyrimidin-4-yloxy)phenyl]-3-methoxypropenoate (0.546 g, prepared as in Example 1) and potassium carbonate (0.228 g) in DMF (5 ml) at room temperature was added dropwise over 20 minutes a solutionof benzyl alcohol (0.178 g) in DMF (5 ml). After stirring for several days, the reaction mixture was poured into water and then extracted with ether (×3). The combined ether extracts were washed successively with dilute aqueous sodium hydroxide solution (×2) and water (×3) and then dried, filtered and evaporated to give a red/brown oil (0.37 g). Chromatography (eluent ether-hexane, 2:1) afforded the title compound (0.10 g) as a pale yellow gum; $^1$H NMR: δ 3.58 (3H, s), 3.70 (3H, s), 5.40 (2H, s), 6.10 (1H, s), 7.14–7;18 (1H, d), 7.25–7.46 (8H, m), 7.45 (1H, s), 8.45 (1H, s) ppm; IR maxima: 1708, 1637 cm$^{-1}$.

EXAMPLE 13

This Example illustrates the preparation of (E)-methyl 2-{2-[6-(2-hydroxythiobenzamido)pyrimidin-6-yloxy]phenyl}-3-methoxypropenoate (Compound No. 367 of Table I).

(E)-Methyl 2-[2-(6-chloropyrimidin-4-yloxy)phenyl]-3-methoxypropenoate (1.50 g, 4.68 mmol) was heated overnight at 95–100° C. with 2-cyanophenol (0.61 g, 5.15 mmol) and potassium carbonate (0.71 g, 5.15 mmol) in DMF (35 ml) in the presence of a catalytic amount of copper(I) chloride. The reaction mixture was cooled, diluted with water and then extracted with ether. The combined ether layers were washed successively with 2H aqueous. sodium hydroxide solution and brine and then dried. Evaporation of the solvent gave a pale yellow oil (1.52 g). Crystallisation from ether/dichloromethane/n-hexane gave (E)-methyl 2-[2-(6-(2-cyanophenoxy)pyrimidin-4-yloxy)phenyl]-3-methoxypropenoate as a pale yellow powder (1.20 g, 64% yield), m.p. 110–111° C.; $^1$H NMR: δ 3.63 (3H, s), 3.74 (3H, s), 6.42 (1H, s), 7.19–7.47 (6H, m), 7.50 (1H, s), 7.62–7.75 (2H, m), 8.40 (1H, s) ppm. In a subsequent preparation of this compound, recrystallisation gave a white crystalline solid, mp 118–119° C.

Excess hydrogen sulphide gas was bubbled through a stirred solution of (E)-methyl 2-[2-(6-(2-cyanophenoxy)pyrimidin-4-yloxy)phenyl]-3-methoxypropenoate (2.09 g, 15.19 mmol) and triethylamine (0.52 g) in dry pyridine (45 ml) at 50° C. After 4½ hours at 50° C. and one week at room temperature, excess hydrogen sulphide was removed by passing air through the reaction mixture. The resulting brown solution was evaporated and azeotroped with toluene (2.50 ml) to give a brown oil, which was triturated with water (3×40 ml). The residue was chromatographed (eluent acetone-hexane, 2:3) to afford a pale yellow oil (0.79 g). Trituration with hexane gave (E)-methyl 2-[2-(6-(2-thiocarboxamidophenoxy)pyrimidin-4-yloxy)phenyl]-3-methoxypropenoate as a pale orange powder (0.68 g, 30% yield); m.p. 125–128° C. A sample prepared subsequently had m.p. 131–3° C.; $^1$H NMR: δ 3.63 (3H, s), 3.78 (3H, s), 6.27 (1H, s), 7.18 (1H, s), 7.10–7.60 (6H, m), 7.49 (1H, s), 7.71 (1H, s), 7.91 (1H, s), 8.05 (1H, dd), 8.39 (1H, s) ppm.

A suspension of (E)-methyl 2-[2-(6-(2-thiocarboxamidophenoxy)pyrimidin-4-yloxy)phenyl]-3-methoxypropenoate (0.437 g) in saturated aqueous sodium hydrogen carbonate solution (50 ml) was stirred at room temperature. After several days dilute aqueous sodium hydroxide (20 ml) was added and stirring at room temperature was continued. After 3 hours, the reaction mixture was washed with ether, acidifed with dilute hydrochloric acid (which gave a yellow suspension) and then extracted with ethyl acetate. The ethyl acetate extracts were washed with water, dried and concentrated to give an orange foam (0.30 g). Chromatography (eluent ethyl acetate) afforded the title compound as a yellow/orange solid (0.1 g); m.p. 104–8° C.; $^1$H NMR: δ 3.62 (3H, s), 3.76 (3H, s), 6.94–7.06 (2H, m), 7.21–7.47 (7H, m), 7.48 (1H, s), 7.61–7.70 (1H, br.s), 8.40–8.50 (1H, br.s), 8.55 (1H, s) ppm; IR maxima: 1701, 1631 cm$^{-1}$.

EXAMPLE 14

This Example illustrates the preparation of (E)-methyl 2-[2-(6-(2-hydroxybenzamido)pyrimidin-4-yloxy)phenyl]-3-methoxypropenoate (Compound No.362 of Table I).

To (E)-methyl 2-[2-(6-(2-cyanophenoxy)pyrimidin-4-yloxy)phenyl]-3-methoxypropenoate (0.46 g, prepared as described in Example 13) in DMSO (2 ml) at room temperature was added potassium carbonate (0.076 g) in water (0.1 ml) followed by hydrogen peroxide (0.2 ml, 30% aqueous solution). After stirring for 4.75 hours, water was added to the reaction mixture producing a creamy precipitate. The precipitate was filtered off, washed with water and dried to afford a cream solid (0.22 g). The filtrate was extracted with ether (×3) and the combined ether extracts were washed with brine and water (×3), and then dried, filtered and evaporated to give a white gum (0.08 g). Chromatography (eluent ether-methanol mixtures) gave the title compound (36 mg) as an off-white foam; m.p. 60–80° C. (softens); $^1$H NMR: δ 3.62 (3H, s), 3.75 (3H, s), 6.94–6.99 (1H, t), 7.04–7.07 (1H, d), 7.20–7.24 (1H, d), 7.30–7.54 (4H, m), 7.47 (1H, s), 7.59–7.63 (1H, m), 7.75 (1H, s), 8.49 (1H, s), 8.80 (1H, s), 11.55 (1H, s) ppm; IR maxima: 3300, 1708, 1686 cm$^{-1}$; mass spectrum m/e 421 (M$^+$) and a second product (E)-methyl 2-[2-(6-(2-carboxamidophenoxy)pyrimidin-4-yloxy)phenyl]-3-methoxypropenoate (0.06 g) as a fluffy white solid which on trituration gave a white crystalline solid; m.p. 138–141° C.; $^1$H NMR: δ 3.60 (3H, s), 3.75 (3H, s), 5.72–5.80 (1H, s), 6.26 (1H, s), 6.60–6.68 (1H, s), 7.12–7.22 (2H, m), 7.28–7.44 (4H, m), 7.46(1H, s), 7.52–7.58 (1H, m), 8.03–8.06 (1H, m), 8.42 (1H, s) ppm; IR maxima: 3480–3190, 1705, 1677 cm$^{-1}$.

EXAMPLE 15

This Example illustrates the preparation of (E)-methyl 2-[2-(6-(2-hydroxyanilino)pyrimidin-4-yloxy)phenyl]-3-methoxypropenoate (Compound No.379 of Table I).

To a solution of (E)-methyl 2-[6-(2-nitrophenoxy)pyrimidin-4-yloxy)phenyl]-3-methoxypropenoate (4.23 g, prepared by the method described for (E)-methyl 2-[2-(6-(2-cyanophenoxy)pyrimidin-4-yloxy)phenyl]-3-methoxypropenoate in Example 13) in acetone (100 ml) at room temperature was added dropwise over several hours an aqueous solution of titanium trichloride (50 ml, 15%). The reaction mixture was stirred for 4 hours, left to stand overnight, and then poured carefully into saturated aqueous sodium hydrogen carbonate (1.251). The resulting mixture was filtered and then extracted with ethyl acetate (×3). The combined organic extracts were washed with brine (×2), dried and evaporated to afford a brown gum (0.72 g). Treatment of a hot ethyl acetate solution of the gum with charcoal led to a yellow foam (0.60 g) which was chromatographed (eluent ethyl acetate-hexane, 2:1) to give the title compound (0.30 g) as a pale yellow solid; m.p. 81–5° C.; $^1$H NMR: δ 3.60 (3H, s), 3.75 (3H, s), 5.93 (1H, s), 6.72 (1H, s), 6.82–6.89 (1H, m), 7.01–7.19 (4H, m), 7.25–7.41 (3H, m), 7.45 (1H, s), 8.35(1H, s), 9.50–9.61 (1H, s) ppm; IR maximum: 1707 cm$^{-1}$.

EXAMPLE 16

This Example illustrates the preparation of (E)-methyl 2-[6-(α-cyanobenzyloxy)pyrimidin-4-yloxy)phenyl]-3-methoxypropenoate (Compound No. 369 of Table I).

To a stirred solution of mandelonitrile (290 mg) in DMF (5 ml) at room temperature was added potassium carbonate (400 mg) followed by (E)-methyl 2-[2-(6-methanesulphonylpyrimidin-4-yloxy)phenyl]-3-methoxypropenoate (530 mg, prepared as described in Example 1). The reaction mixture was stirred at room temperature for 6 hours, poured into water (20 ml) and then extracted with ether (×3). The combined ether layers were dried, filtered and evaporated. The residue was combined with a second preparation and then chromatographed (eluent ether-hexane, 3:1) to afford the title compound. as an oil (97 mg); $^1$H NMR: δ 3.55 (3H, s), 3.70 (3H, s), 6.15 (1H, s), 6.80 (1H, s), 7.15 (1H, d), 7.28–7.50 (6H, m), 7.45 (1H, s), 7.60 (2H, m), 8.50 (1H, s) ppm; mass spectrum m/e 417 (M$^+$).

EXAMPLE 17

This Example illustrates the preparation of (E)-methyl 2-[2-(6-(2-cyanobenzenesulphonyloxy)pyrimidin-4-yloxy)phenyl]-3-methoxypropenoate (Compound No. 381 of Table I).

To a solution of 4-nitrobenzyl alcohol (666 mg) in DMF (8 ml) was added potassium carbonate (800 mg) followed by a solution of (E)-methyl 2-[2-(6-methanesulphonyl-pyrimidin-4-yloxy)phenyl]-3-methoxypropenoate (1.0 g, prepared as described in Example 1) in DMF (3 ml). The reaction mixture was heated to 60° C. under an atmosphere of nitrogen for 5½ hours, cooled and then poured into water (40 ml). The resulting mixture was extracted with ether (×3) and the combined ether layers were dried and evaporated to yield an orange oil. Chromatography (eluent ether-hexane, 7:3) gave (E)-methyl 2-[2-(6-(4-nitrobenzyloxy)pyrimidin-4-yloxy)phenyl]-3-methoxypropenoate (532 mg) as a glass which solidified on standing; m.p. 96–98° C.; $^1$H NMR: δ 3.55 (3H, s), 3.75 (3H, s), 5.50 (2H, s), 6.15 (1H, s), 7.15 (1H, d), 7.3 (3H, m), 7.45 (1H, s), 7.58 (2H, d), 8.22 (2H, d), 8.42 (1H, s) ppm; IR maxima: 1700, 1620, 1560, 1340 cm$^{-1}$; mass spectrum m/e 437 (M$^+$).

(E)-Methyl 2-[2-(6-(4-nitrobenzyloxy)pyrimidin-4-yloxy)phenyl]-3-methoxypropenoate (1.4 g) in ethanol (30 ml) in the presence of 5% Pd/C catalyst (300 mg) was treated with hydrogen at 1 atmosphere pressure. After 90 minutes, the reaction mixture was filtered and evaporated to give a yellow oil. Chromatography (eluent ethyl acetate-hexane, 95:5) afforded (E)-methyl 2-[2-(6-hydroxypyrimidin-4-yloxy)phenyl]-3-methoxypropenoate (500 mg) as a pale yellow solid; m.p. 168–170° C.; $^1$H NMR: δ 3.80 (3H, s), 5.65 (1H, s), 7.15 (1H, d), 7.3 (3H, m), 7.50 (1H, s), 7.95 (1H, s) ppm; IR maximum: 1680cm$^{-1}$; mass spectrum m/e 302 (M$^+$).

To a solution of (E)-methyl 2-[2-(6-hydroxypyrimidin-4-yloxy)phenyl]-3-methoxypropenoate (315 mg) in pyridine (3 ml) was added 2-cyanobenzenesulphonyl chloride (505 mg) in one portion. The reaction mixture was stirred at room temperature for 5 hours, left to stand overnight and then poured into water (15 ml). The resulting mixture was extracted with dichloromethane (×2) and the combined organic layers were washed with water, dried, filtered and evaporated to give a gum. Trituration with ether gave the title compound (250 mg) as a solid; m.p. 151–2° C.; $^1$H NMR: δ 3.6 (3H, s), 3.7 (3H, s), 6.52 (1H, s), 7.15 (1H, d), 7.3 (3H, m), 7.45 (1H, s), 7.85 (2H, m), 7.95 (1H, m), 8.25 (1H, d), 8.42 (1H, s) ppm; IR maxima 2240, 1700 cm$^{-1}$; mass spectrum m/e 467 (M$^+$).

EXAMPLE 18

This Example illustrates the preparation of (E)-methyl 2-[2-(6-(2-cyanobenzyloxy)pyrimidin-4-yloxy)phenyl]-3-methoxypropenoate (Compound No. 389 of Table I).

To a solution of (E)-methyl 2-[2-(6-hydroxypyrimidin-4-yloxy)phenyl]-3-methoxypropenoate (500 mg, prepared according to the method outlined in Example 17) in DMF (3 ml) was added potassium carbonate (270 mg). The mixture was stirred at room temperature for 30 minutes and then a solution of 2-cyanobenzyl bromide (345 mg) in DMF (3 ml) was added. The reaction mixture was stirred at room temperature for 3 hours and then poured into water (15 ml) and extracted with dichloromethane (×3). The combined organic extracts were dried and concentrated. Chromatography of the residue (eluent ethyl acetate-hexane, 8:2) gave the title compound (83 mg) as a gum; $^1$H NMR: δ 3.55 (3H, s), 3.72 (3H, s), 5.60 (2H, s), 6.15 (1H, s), 7.15(1H, d), 7.25–7.50 (4H, m), 7.45 (1H, s), 7.60 (2H, m), 7.70 (1H, d), 8.45 (1H, s) ppm; IR maxima: 2240, 1700, 1630 cm$^{-1}$.

EXAMPLE 19

This Example illustrates the preparation of (E)-methyl 2-[2-(6-(benzthiazol-2-ylthio)pyrimidin-4-yloxy)phenyl]-3-methoxypropenoate (Compound No. 530 of Table I).

To a stirred suspension of sodium hydride (150 mg, 3.43 mmol, 55% dispersion in oil, pre-washed with petroleum ether) in DMF (4 ml) was added drapwise a solution of 2-mercaptobenzthiazole (521 mg, 3.12 mmol) in DMF (8 ml). Effervescence took place and the reaction mixture became tan-coloured. After stirring at room temperature for 10 minutes, the reaction mixture was heated at 60° C. for 30 minutes and then cooled again to room temperture. A solution of (E)-methyl 2-[2-(6-chloropyrimidin-4-yloxy) phenyl]-3-methoxypropenoate (1.00 g, 3.12 mmol) in DMF (8 ml) was then added over a period of one minute. The reaction mixture was cooled, poured into vater and extracted with ether (×3). The combined ether extracts were washed with water (×3), dried and evaporated to give a brown gum (424 mg). Chromatography (eluent ether-hexane, 3:2) afforded the title compound as an opaque cream gum (124 mg, 8%); IR maxima 3050, 2947, 1709, 1633 cm$^{-1}$; mass spectrum: m/e 451 (M$^+$); $^1$H NMR: δ 3.58 (3H, s), 3.72 (3H, s), 7.16 (1H, d), 7.44 (1H, s), 7.27–7.56 (5H, m), 7.89 (1H, d), 7.91 (1H, s), 8.06 (1H, d), 8.64 (1H, s) ppm.

EXAMPLE 20

This Example illustrates the preparation of (E)-methyl 2-[2-(6-benzylpyrimidin-4-yloxy)phenyl]-3-methoxypropenoate (Compound No. 9 of Table I).

A solution of (E)-methyl 2-[2-(6-chloropyrimidin-4-yloxy)phenyl]-3-methoxypropenoate (0.6 g), benzyl tri-n-butyltin (0.75 g) and bis(triphenylphosphine)palladium chloride (0.1 g) in DMF (20 ml) was heated at 100° C. for 16 hours. The reaction mixture was cooled to room temperature and potassium fluoride (20 ml of a 10% aqueous solution) was added. The resulting mixture was stirred for 3 hours then filtered through 'Hyflo' supercel filter aid which was rinsed through with ether. The combined filtrates and washings were extracted with ether (×2) and the combined extracts were washed with brine, then dried, concentrated and chromatographed using ether:hexane 1:1 as the eluent to give the title compound (0.4 g), containing as a 50% impurity (E)-methyl 2-[2-n-butylpyrimidin-4-yloxy) phenyl]-3-methoxypropenoate, as an oil; $^1$H NMR: δ 4.04 (2H, s, $C_6H_5$-C$\underline{H}_2$), 7.40 or 7.44 (1H, s) ppm.

EXAMPLE 21

This Example illustrates the preparation of Compound No. 404 of Table I.

A solution of 2-acetylpyrazine oxime (0.50 g) in DMF (15 ml) was added dropvise to a stirred suspension of sodium hydride (88 mg) in DMF (10 ml). After 15 minutes, a solution of (E)-methyl 2-[2-(6-chloropyrimidin-4-yloxy) phenyl]-3-methoxypropenoate (1.17 g) in DMF (25 ml) was added, and the resulting mixture was stirred at room temperature for 3 hours. The reaction mixture was diluted with water and extracted with ether. The ether extracts were washed with water, dried, concentrated and chromatographed using ethyl acetate as eluent to give the title compound (0.52 g, 34% yield) as an orange gum which crystallised on standing, m.p. 138–40° C; $^1$H NMR: δ 2.62 (3H, s), 3.59 (3H, s), 3.73 (3H, s), 6.81 (1H, s), 7.48 (1H, s), 8.51 (1H, s), 8.64 (2H, s), 9.26 (1H, s) ppm; IR maximum: 1708 cm$^{-1}$.

The following are examples of compositions suitable for agricultural and horticiultural purposes which can be formulated from the compounds of the invention. Such compositions form another aspect of the invention. Percentages are by weight.

EXAMPLE 22

An emulsifiable concentrate is made up by mixing and stirring the ingredients until all are dissolved.

| | |
|---|---|
| Compound No. 180 of Table II | 10% |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 23

The active ingredient is dissolved in methylene dichloride and the resultant liquid sprayed on to the granules of attapulgite clay. The solvent is then allowed to evaporate to produce a granular composition.

| | |
|---|---|
| Compound No. 180 of Table II | 5% |
| Attapulgite granules | 95% |

EXAMPLE 24

A composition suitable for use as a seed dressing is prepared by grinding and mixing the three Ingredients.

| | |
|---|---|
| Compound No. 180 of Table II | 50% |
| Mineral oil | 2% |
| China clay | 48% |

EXAMPLE 25

A dustable powder is prepared by grinding and mixing the active ingredient with talc.

| | |
|---|---|
| Compound No. 180 of Table II | 5% |
| Talc | 95% |

EXAMPLE 26

A suspension concentrate is prepared by ball milling the ingredients to form an aqueous suspension of the ground mixture with water.

| | |
|---|---|
| Compound No. 180 of Table II | 40% |
| Sodium lignosulphonate | 10% |
| Bentonite clay | 1% |
| Water | 49% |

This formulation can be used as a spray by diluting into water or applied directly to seed.

EXAMPLE 27

A wettable powder formulation is made by mixing together and grinding the ingredients until all are throughly mixed.

| | |
|---|---|
| Compound No. 212 of Table I | 25% |
| Sodium lauryl sulphate | 2% |
| Sodium lignosulphonate | 5% |
| Silica | 25% |
| China clay | 43% |

EXAMPLE 28

The compounds were tested against a variety of foliar fungal diseases of plants. The technique employed was as follows.

The plants were grown in John Innes Potting Compost (No.1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient except where otherwise indicated) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control vas recorded by the following grading:

4=no disease
3=trace-5% of disease on untreated plants
2=6-25% of disease on untreated plants
1=26-59% of disease on untreated plants
0=60-100% of disease on untreated plants The results are shown in Table IX.

Key to Diseases

Pr *Puccinia recondita*
Egh *Erysiphe graminis hordei*
Egt *Erysiphe graminis tritici*
Sn *Septoria nodorum*
Po *Pyricularia oryzae*
Tc *Thanatephorus cucumeris*
Vi *Venturia inaegualis*
Ca *Cercospora arachidicola*

Pv Plasmopara viticola
Pil Phytophthora infestans lycopersici

TABLE IX

| Compound No | Table No | Pr | Egh | Egt | Sn | Po | Tc | Vi | Ca | Pv | Pil |
|---|---|---|---|---|---|---|---|---|---|---|---|
| 1 | I | 4 | 4 | — | — | 4 | — | 4 | — | 4 | 4 |
| 2 | I | 0ª | 0ª | — | — | 0ª | — | 0ª | — | 4ª | 0ª |
| 3 | I | 3 | 0 | — | — | 2 | — | 4 | — | 4 | 0 |
| 4 | I | 4 | 4 | — | — | 3 | — | 4 | 4 | 4 | 3 |
| 9 | I | 0 | — | 4 | 4 | 4 | — | 4 | — | 4 | 4 |
| 23 | I | 4 | 4 | — | — | 4 | — | 4 | 4 | 4 | 4 |
| 96 | I | 4 | 4 | — | — | 3 | — | — | — | 4 | 4 |
| 133 | I | 4 | 4 | — | — | 3 | 4 | 3 | — | 4 | 0 |
| 134 | I | 4 | 4 | — | — | 2 | — | — | — | 4 | — |
| 180 | I | 4 | 4 | — | — | — | — | 4 | 4 | 4 | — |
| 218 | I | 4 | 4 | — | — | 3 | — | 4 | 4 | 4 | 3 |
| 220 | I | 4 | 4 | — | — | 4 | — | 4 | 4 | 4 | 0 |
| 222 | I | 4 | — | 4 | 3 | 4 | — | 4 | — | 4 | 0 |
| 229 | I | 4 | — | 4 | 4 | 4 | — | 4 | — | 4 | 3 |
| 236 | I | 4 | — | 3 | 3 | 2 | — | 4 | — | 4 | 4 |
| 239 | I | 4 | 4 | — | — | 3 | — | 4 | 4 | 4 | 4 |
| 250 | I | — | — | 4 | 4 | 2 | — | — | — | 4 | — |
| 271 | I | 4 | — | 3 | 2 | 2 | — | 0 | — | 0 | 2 |
| 320 | I | 4 | — | 4 | 4 | 3 | 4 | — | 4 | 4 | 4 |
| 354 | I | 4 | 4 | — | — | 3 | — | 4 | 4 | 4 | 0 |
| 355 | I | 0 | 4 | — | — | — | — | 4 | — | 0 | 0 |
| 356 | I | 1 | 0 | — | — | — | — | 4 | 3 | 4 | 0 |
| 357 | I | 4 | 4 | — | — | 4 | — | 4 | — | 4 | 4 |
| 358 | I | 4 | 4 | — | — | 4 | — | 4 | — | 4 | 4 |
| 359 | I | 4 | 4 | — | — | — | — | — | 4 | 4 | 4 |
| 360 | I | 4 | 4 | — | — | 4 | — | 4 | — | 4 | 4 |
| 361 | I | 4 | 4 | — | — | 4 | — | 4 | — | 4 | 4 |
| 363 | I | 4 | 4 | — | — | 4 | — | 4 | — | 4 | 4 |
| 364 | I | 4 | 4 | — | — | 4 | — | 4 | — | 4 | 4 |
| 365 | I | 4 | 4 | — | — | 4 | — | 4 | — | 4 | 4 |
| 366 | I | 4 | 4 | — | — | 4 | — | 4 | — | 4 | 4 |
| 367 | I | 4ª | 3ª | — | — | 0ª | — | 2ª | — | 4ª | 0ª |
| 368 | I | 4 | 4 | — | — | 3 | — | 4 | — | 4 | 3 |
| 369 | I | 4 | 4 | — | — | 4 | — | 4 | — | 4 | 3 |
| 370 | I | 4 | 4 | — | — | 4 | — | 4 | — | 4 | 4 |
| 371 | I | 4 | 4 | — | — | 4 | — | 4 | — | 4 | 0 |
| 372 | I | 4 | 4 | — | — | 4 | — | 4 | — | 4 | 4 |
| 373 | I | 4 | 4 | — | — | 4 | — | 4 | — | 4 | 3 |
| 374 | I | 4 | 4 | — | — | 4 | — | 4 | — | 4 | 4 |
| 375 | I | 4 | 4 | — | — | 4 | 4 | 3 | — | 3 | 0 |
| 376 | I | 4 | 4 | — | — | 3 | 4 | 4 | — | 4 | 4 |
| 377 | I | 4 | 4 | — | — | 0 | — | 4 | 4 | 4 | 4 |
| 379 | I | 3 | 0 | — | — | 0 | — | o | — | 4 | 0 |
| 380 | I | 4 | 4 | — | — | 4 | — | 4 | — | 4 | 3 |
| 381 | I | 2 | 0 | — | — | 2 | — | 0 | — | 0 | 0 |
| 382 | I | 4 | 4 | — | — | 4 | — | 4 | — | 4 | 4 |
| 383 | I | 4ª | 0ª | — | — | 4ª | 0ª | 4ª | 3ª | 4ª | 0ª |
| 384 | I | 4 | 4 | — | — | 4 | — | 4 | — | 4 | 4 |
| 385 | I | 4 | 4 | — | — | 4 | — | 4 | — | 4 | 4 |
| 386 | I | 4 | 4 | — | — | 4 | 4 | 4 | — | 4 | 4 |
| 387 | I | 4 | 4 | — | — | 4 | 4 | 4 | — | 4 | 4 |
| 388 | I | 4 | 4 | — | — | 4 | 4 | 4 | — | 4 | 4 |
| 389 | I | 4ª | 4ª | — | — | 4ª | 4ª | 4ª | — | 4ª | 0ª |
| 390 | I | 4 | 3 | — | — | 3 | 4 | 1 | — | 4 | 0 |
| 391 | I | 4 | 4 | — | — | 4 | 3 | 4 | — | 4 | 4 |
| 392 | I | 0ª | 0ª | — | — | 1ª | 0ª | 0ª | — | 0ª | 0ª |
| 393 | I | 4 | 4 | — | — | 4 | 4 | 0 | — | 4 | 4 |
| 394 | I | 4 | — | 4 | 4 | 3 | 4 | — | — | 4 | 4 |
| 395 | I | 4 | — | 4 | 3 | 4 | — | 4 | — | 4 | — |
| 396 | I | 4 | — | 4 | 4 | 4 | — | 3 | — | 4 | 4 |
| 397 | I | 4 | — | 4 | 3 | 4 | — | 4 | — | 4 | 3 |
| 398 | I | 4 | 4 | — | — | 3 | — | 4 | 4 | 4 | 4 |
| 399 | I | 0ª | — | 0ª | 0ª | 0ª | — | 3ª | — | 4ª | 0ª |
| 400 | I | 4 | — | 4 | 4 | 0 | — | 4 | — | 4 | 4 |
| 401 | I | 4 | — | 4 | 4 | 0 | — | 4 | — | 4 | 3 |
| 402 | I | 4 | — | 4 | 4 | 0 | — | 4 | — | 4 | 3 |
| 403 | I | 4ᵇ | — | 0ª | 0ª | 0ª | — | 4ª | — | 4ª | 1ª |
| 404 | I | 4 | — | 4 | 3 | 3 | — | 4 | — | 4 | 1 |
| 405 | I | 4 | — | 4 | 4 | 0 | — | 4 | — | 4 | 4 |
| 406 | I | 0 | — | 1 | 0 | 0 | 0 | 1 | — | 4 | 0 |
| 407 | I | 0ª | — | 1ª | 0ª | 1ª | 0ª | 3ª | — | 4ª | 0ª |
| 530 | I | 3 | — | 4 | 4 | 0 | — | 4 | — | 4 | 4 |
| 180 | II | 4 | 4 | — | — | 2 | — | 4 | — | 4 | 4 |

TABLE IX-continued

| Compound No | Table No | Pr | Egh | Egt | Sn | Po | Tc | Vi | Ca | Pv | Pil |
|---|---|---|---|---|---|---|---|---|---|---|---|
| 378 | II | 4 | 4 | — | — | 3 | — | 4 | — | 4 | 4 |
| 180 | III | 4ª | 4ª | — | — | 3ª | — | 4ª | 3ª | 4ª | 4ª |

ª10 ppm foliar application only
ᵇ100 ppm foliar application only
— no result

CHEMICAL FORMULAE
(in description)

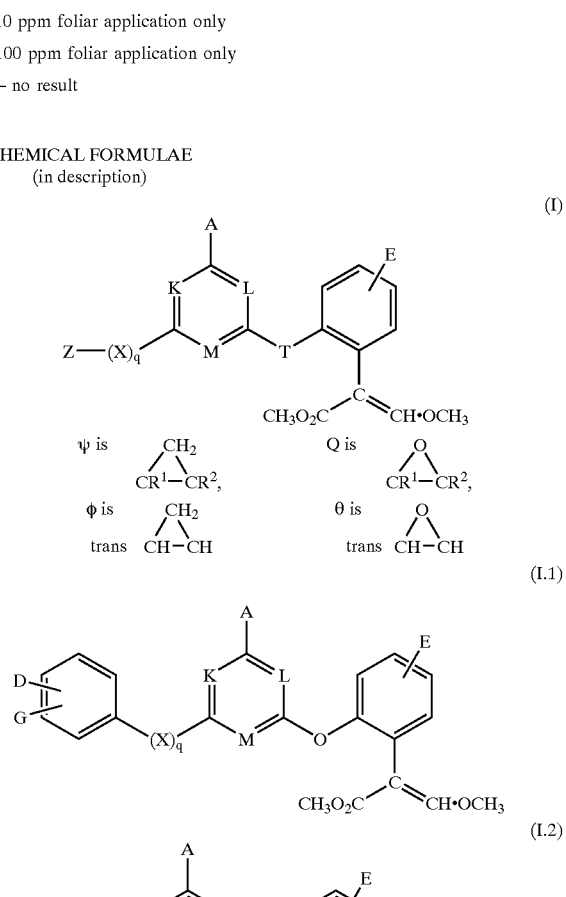

(I)

(I.1)

(I.2)

* X for Compound No 117 is

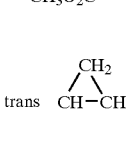

* X for Compound No 118 is

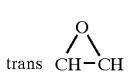

* Z for Compound No 353 is

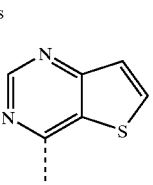

* Z for Compound No 418 is
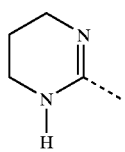
* Z for Compound No 421 is
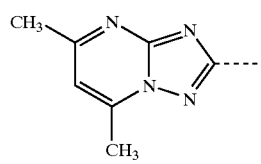
* Z for Compounds Nos 513 and 514 is
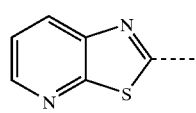
* Z for Compounds Nos 515 and 516 is
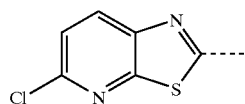
TABLE I
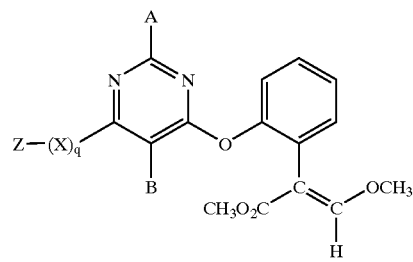
(I.3)
TABLE II
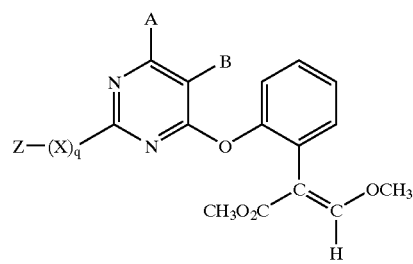
(I.4)
TABLE III
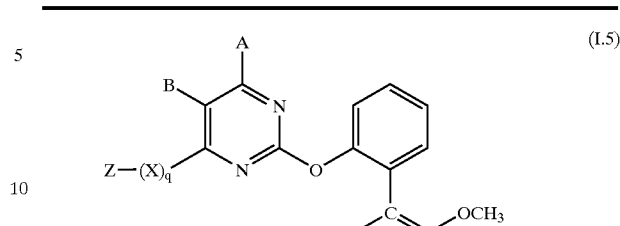
(I.5)
TABLE IV
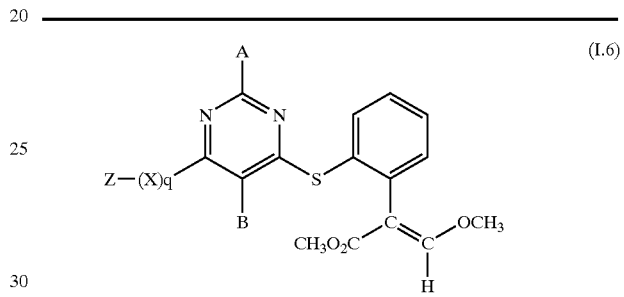
(I.6)
TABLE V
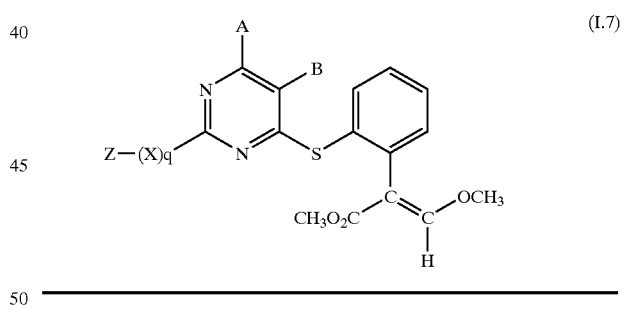
(I.7)
TABLE VI
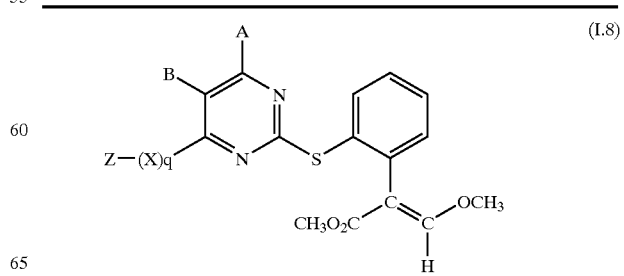
(I.8)

Scheme I

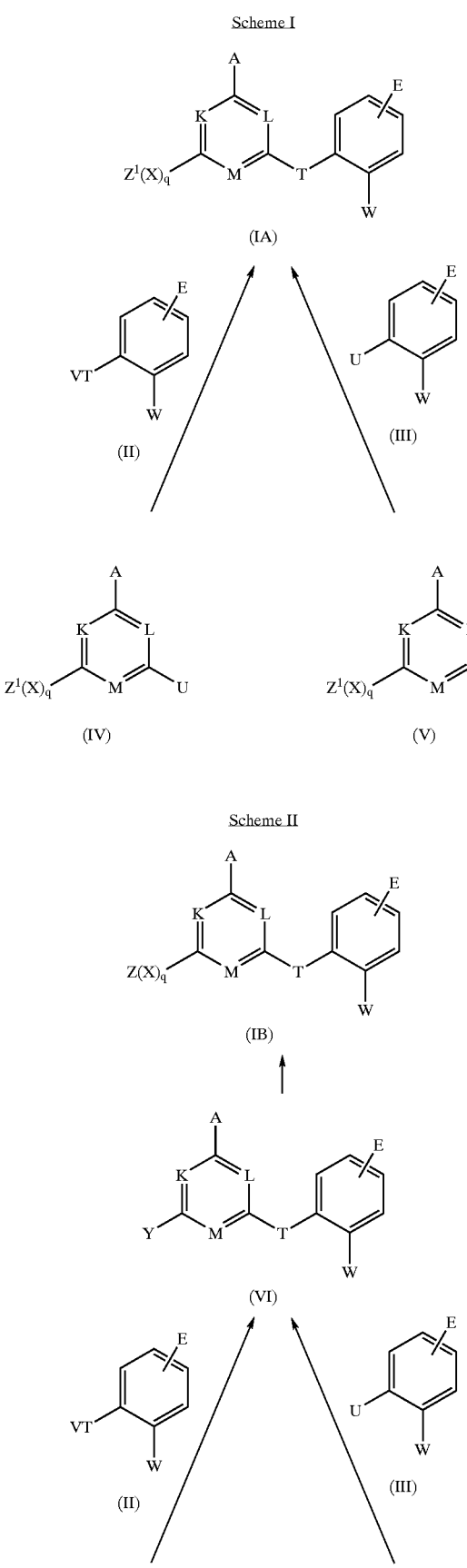

Scheme II

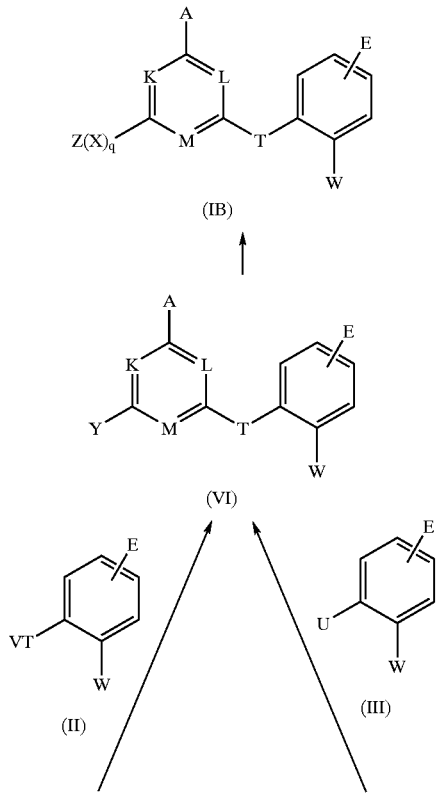

-continued

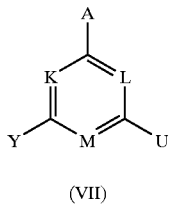
(VII)

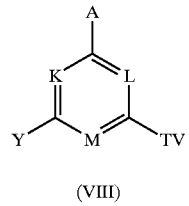
(VIII)

What is claimed is:

1. A compound of formula (I) or a stereoisomer thereof:

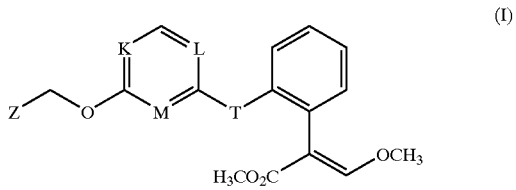
(I)

wherein any two of K, L and M are nitrogen and the other is CH;

T is oxygen or sulfur;

Z is an optionally substituted phenyl group or an optionally substituted heterocyclyl group selected from the group consisting of pyridinyl, pyrimidinyl, pyrazinyl, pyridazinyl, 1,2,3-triazinyl, 1,2,4-triazinyl, 1,3,5-triazinyl, 1,2,4,5-tetrazinyl, 1,2,3-triazolyl, 1,2,4-triazolyl, imidazolyl, thienyl, furyl, pyrrolyl, pyrazolyl, thiazolyl, isothiazolyl, oxazolyl, isoxazolyl, 1,2,4-thiadiazolyl, 1,3,5-thiadiazolyl, oxadiazolyl, piperidinyl, morpholinyl, pyrrolidinyl and tetrahydrofuranyl, and, where appropriate, the corresponding N-oxides;

the substituents when Z is the substituted phenyl group or the substituted heterocyclyl group are selected from one or more of the following: halo, hydroxy, oxo, mercapto, $C_{1-4}$ alkyl, $C_{2-4}$ alkenyl, $C_{2-4}$-alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, $C_{2-4}$alkenylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, phenyl, phenoxy, $C_{1-4}$ alkanoyloxy, cyano, isocyano, thiocyanato, isothiocyanato, nitro, —NR'R", —N$_3$, —NHCONR'R", —NR'COR", CONR'R", CR'=NOR", CHR'CO$_2$R", CSNR'R', —CO$_2$R', —OSO$_2$R', —SO$_2$R'—SOR', SO$_2$OR', SO$_2$NR'R", —COR', —OCOR', —CR'=NR", N=CHNR'R", NHSO$_2$R' or N=CR'R" in which R' and R" are independently hydrogen, hydroxy, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$) alkyl, $C_{2-4}$-alkenyl, $C_{2-4}$ alkenyloxy, phenyl, phenoxy or benzyl, wherein the phenyl, phenoxy and benzyl groups are optionally substituted with halogen, $C_{1-4}$ alkyl or $C_{1-4}$ alkoxy, or when Z is the substituted phenyl group or the substituted heterocyclyl group two adjacent substituents of Z join to form a benzene ring.

2. The compound of claim 1, wherein T is oxygen.

3. The compound of claim 1, wherein K is nitrogen, L is nitrogen and M is CH.

4. The compound of claim 1, wherein T is oxygen and Z is an optionally substituted heterocyclyl group.

5. The compound of claim 1, wherein K is nitrogen; L is nitrogen; M is CH; T is oxygen; and Z is an unsubstituted phenyl group; a 3-fluoro phenyl group; a 2-methoxy phenyl group; a 4-nitro phenyl group; a 3-bromo phenyl group; a 2-phenoxy phenyl group; a 4-ethoxy phenyl group; a 2,4-dichloro phenyl group; a 2-chloro-3-methoxy phenyl group; a 3-chloro-5-methoxy phenyl group; a 2-(E)-(CH$_3$O$_2$C—C=CH—OCH$_3$) phenyl group; a 3-cyano-4,6-difluoro phenyl group; a 2,6-difluoro phenyl group; a 2-nitro phenyl group; a 2-chloro-6-CF$_3$ phenyl group; a 2-CF$_3$ phenyl group; a 2-tluoro-6-chloro phenyl group; a 4-fluoro phenyl group; a 2-cyano phenyl group; a 1-naphthyl group; a pyridin-2-yl group; a pyridin-3-yl group; a pyridin-4-yl group; a pyrimidin-2-yl group; a pyrimidin-4-yl group; a pyrimidin-5-yl group; a pyrazin-2-yl group; a pyridazin-3-yl group; a pyridazin-4-yl group; a 1,2,4-triazin-6-yl group; a quinolin-2-yl group; a benzthiazol-2-yl group; a thien-3-yl group; a purin-6yl group; a furan-2-yl group; a 3-methyl-pyridin-2-yl group; a 4-cyanopyrimidin-2-yl group; a 2-CH$_3$S-pyrimidin-4-yl group; a pyrimidin-2-yl,1-N-oxide group; a C$_6$F$_5$ group; or a thien-2-yl group.

6. The compound of claim 1, wherein K is nitrogen; M is nitrogen; L is CH; T is oxygen; and Z is an unsubstituted phenyl group; a 3-fluoro phenyl group; a 2-methoxy phenyl group; a 4-nitro phenyl group; a 3-bromo phenyl group; a 2-phenoxy phenyl group; a 4-ethoxy phenyl group; a 2,4-dichloro phenyl group; a 2-chloro-3-methoxy phenyl group; a 3-chloro-5-methoxy phenyl group; a 2-(E)-(CH$_3$O$_2$C—C=CH—OCH$_3$) phenyl group; a 3cyano-4,6-difluoro phenyl group; a 2,6-didluoro phenyl group; a 2-nitro phenyl group; a 2-chloro-6-CF$_3$ phenyl group; a 2-CF$_3$ phenyl group; a 2-fluoro-6-chloro phenyl group; a 4-fluoro phenyl group; a 2-cyano phenyl group; a 1-naphthyl group; a pyridin-2-yl group; a pyridin-3-yl group; a pyridin-4-yl group; a pyrimidin-2-yl group; a pyrimidin-4-yl group; a pyrimidin-5-yl group; a pyrazin-2-yl group; a pyridazin-3-yl group; a pyridazin-4-yl group; a 1,2,4-triazin-6-yl group; a quinolin-2-yl group; a benzthiazol-2-yl group; a thien-3-yl group; a purin-6-yl group; a furan-2-yl group; a 3-methyl-pyridin-2-yl group; a 4-cyanopyrimidin-2-yl group: a 2-CH$_3$S-pyrimidin-4-yl group; a pyrimidin-2-yl,1-N-oxide group; a C$_6$F$_5$ group; or a thien-2-yl group.

7. The compound of claim 1, wherein K is CH: M is nitrogen; L is nitrogen; T is oxygen; and Z is an unsubstituted phenylgroup; a 3-fluoro phenyl group; a 2-methoxy phenyl group; a 4-nitro phenyl group; a 3-bromo phenyl group; a 2-phenoxy phenyl group; a 4-ethoxy phenyl group; a 2,4-dichloro phenyl group; a 2-chloro-3-methoxy phenyl group; a 3-chloro-5-methoxy phenyl group; a 2-(E)-(CH$_3$O$_2$C—C=CH—OCH$_3$) phenyl group; a 3-cyano-4,6-difluoro phenyl group; a 2,6-difluoro phenyl group; a 2-nitro phenyl group; 2-chloro-6-CF$_3$ phenyl group; a 2-cyano phenyl group; a 1-naphthyl group; a pyridin-2-yl group; a pyridin-3-yl group; a pyridin-4-yl group; a pyrimidin-2-yl group; a pyrimidin-4-yl group; a pyrimidin-5yl group; a pyrazin-2-yl group; a pyridazin-3-yl group; a pyridazin-4-yl group; a 1,2,4-triazin-6-yl group; a quinolin-2-yl group; a benzthiazol-2-yl group; a thien-3-yl group; a purin-6-yl group; a furan-2-yl group; a 3-methyl-pyridin-2-yl group; a 4-cyanopyrimidin-2-yl group; a 2-CH$_3$S-pyrimidin-4-yl group; a pyrimidin-2-yl,1-N-oxide group; a C$_6$F$_5$ group; or a thien-2-yl group.

8. The compound of claim 1, wherein K is nitrogen; L is nitrogen; M is CH; T is sulfur; and Z is an unsubstituted phenyl group a 3-fluoro phenyl group; a 2-methoxy phenyl group; a 4-nitro phenyl group; a 3-bromo phenyl group; a 2-phenoxy phenyl group; a 4-ethoxy phenyl group; a 2,4dichloro phenyl group; a 2-chloro-3-methoxy phenyl group; a 3-chloro-5-methoxy phenyl group; a 2-(E)-(CH$_3$O$_2$C—C=CH—OCH$_3$) phenyl group; a 3-cyano-4,6-difluoro phenyl group; a 2,6-difluoro phenyl group; a 2-nitro phenyl group; a 2-chloro-6-CF$_3$ phenyl group; a 2-CF$_3$ phenyl group; a 2-fluoro-6-chloro phenyl group; a 4-fluoro phenyl group; a 2-cyano phenyl group; a 1-naphthyl group; a pyridin-2-yl group; a pyridin-3-yl group; a pyridin-4-yl group; a pyrlmidin-2-yl group; a pyrimidin4-yl group; a pyrimidin-5yl group; a pyrazin-2-yl group; a pyridazin-3-yl group; a pyridazin-4-yl group; a 1,2,4-triazin-6yl group; a quinolin-2-yl group; a benzthiazol-2-yl group; a thien-3-yl group; a purin-6yl group; a furan-2-yl group; a 3-methyl-pyridin-2-yl group; a 4-cyanopyrimidin-2-yl group; a 2-CH$_3$S-pyrimidin-4-yl group; a pyrimidin-2-yl,1-N-oxide group; a C$_6$F$_5$ group; or a thien-2-yl group.

9. The compound of claim 1, wherein K is nitrogen; L is CH; M is nitrogen; T is sulfur; and Z is an unsubstituted phenyl group; a 3-fluoro phenyl group; a 2-methoxy phenyl group; a 4-nitro phenyl group; a 3-bromo phenyl group; a 2-phenoxy phenyl group; a 4-ethoxy phenyl group; a 2,4-dichloro phenyl group; a 2-chloro-3-methoxy phenyl group; a 3-chloro-5-methoxy phenyl group; a 2-(E)-(CH$_3$O$_2$C—=CH—OCH$_3$) phenyl group; a 3-cyano-4,6-difluoro phenyl group; a 2,6-ddluoro phenyl group; a 2-nitro phenyl group; a 2-chloro-6CF$_3$ phenyl group; a 2-CF$_3$ phenyl group; a 2-fluoro-6-chloro phenyl group; a 4-fluoro phenyl group; a 2-cyano phenyl group; a 1-naphthyl group; a pyridin-2-yl group; a pyridin-3-yl group; a pyridin-4-yl group; a pyrimidin-2-yl group; a pyrimidinyl group; a pyrimidin-5-yl group; a pyrazin-2-yl group; a pyridazin-3-yl group; a pyridazin-4-yl group; a 1,2,4-triazin-6-yl group; a quinolin-2-yl group; a benzthiazol-2-yl group; a thien-3-yl group; a purin-6-yl group; a furan-2-yl group; a 3-methyl-pyridin-2-yl group; a 4-cyanopyrimidin-2-yl group; a 2-CH$_3$S-pyrimidin-4-yl group; a pyrimidin-2-yl,1-N-oxide group; a C$_6$F$_5$ group; or a thien-2-yl group.

10. The compound of claim 1, wherein K is CH; L is nitrogen; M is nitrogen; T is sulfur; and Z is an unsubstituted phenyl group; a 3-fluoro phenrryl group; a 2-methoxy phenyl group; a 4-nitro phenyl group; a 3bromo phenyl group; a 2-phenoxy phenyl group; a 4-ethoxy phenyl group; a 2,4-dichloro phenyl group; a 2-chloro-3,methoxy phenyl group; a 3-chloro-5-methoxy phenyl group; a 2-(E)-(CH$_3$O$_2$C—C=CH—OCH$_3$) phenyl group; a 3cyano-4,6-difluoro phenyl group; a 2,6-difluoro phenyl group; a 2-nitro phenyl group; a 2-chloro6CF$_3$ phenyl group; a 2-CF$_3$ phenyl group; a 2-fluoro-6-chloro phenyl group; a 4-fluoro phenyl group; a 2-cyano phenyl group; a 1-naphthyl group; a pyridin-2-yl group; a pyridin-3-yl group; a pyridin-4-yl group; a pyrimidin-2-yl group; a pyrimidinyl group; a pyrimidin-5-yl group; a pyrazin-2-yl group; a pyridazin-3,yl group; a pyridazin-4-yl group; a 1,2,4-triazin-6-yl group; a quinolin-2-yl group; a benzthiazol-2-yl group; a thien-3-yl group; a purin-6-yl group; a furan-2-yl group; a 3,methyl-pyridin-2-yl group; a 4-cyanopyrimidin-2-yl group; a 2-CH$_3$S-pyrimidin-4-yl group; a pyrimidin-2-yl,1-N-oxide group; a C$_6$F$_5$ group; or a thien-2-yl group.

11. A fungicidal composition comprising a fungicidally effective amount of the compound of claim 1 and a fungicidally acceptable carrier or diluent thereof.

12. A method of combating fungi comprising applying to a plant, to a seed of a plant or to a locus of a plant or a seed a fungicidally effective amount of the compound of claim 1.

13. A compound of formula (I) or a stereoisomer thereof:

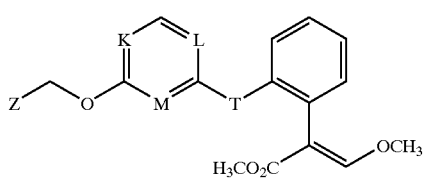

(I)

wherein any two of K, L and M are nitrogen and the other is CH;

T is oxygen or sulfur;

Z is an optionally substituted phenyl group; wherein the substituents are selected from one or more of the following: halo, hydroxy, oxo, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo ($C_{1-4}$) alkyl, halo ($C_{1-4}$) alkoxy, $C_{1-4}$ alkylthio, $C_{2-4}$ alkenylthio, hydroxy ($C_{1-4}$)alkyl, $C_{1-4}$ alkoxy ($C_{1-4}$)alkyl, $C_{3-6}$ cycloalkyl, $C_{3-6}$ cycloalkyl ($C_{1-4}$)alkyl, phenyl, phenoxy, ($C_{1-4}$) alkanoyloxy, cyano, isocyano, thiocyanato, isothiocyanato, nitro, —NR'R", —N$_3$, —NHCONR'R", —NR'COR", —CONR'R, CR'=NOR", CHR'CO$_2$R', CSNR'R', —CO$_2$R', —OSO$_2$R', —SO$_2$R', —SOR', SO$_2$OR', SO$_2$NR'R", —COR', —OCOR', —CR'=NR", N=CHNR'R", NHSO$_2$R' or N=CR'R" in which R' and R" are independently hydrogen, hydroxy, $C_{1-4}$, alkyl, $C_{1-4}$ alkoxy, $C_{1-4}$ alkylthio, $C_{3-6}$ cydoalkyl, $C_{3-6}$ cycloalkyl($C_{1-4}$) alkyl, $C_{2-4}$ alkenyl, $C_{2-4}$ alkenyloxy, phenyl, phenoxy or benzyl, wherein the phenyl, phenoxy and benzyl groups are optionally substituted with halogen, $C_{1-4}$ alkyl or $C_{1-4}$ alkoxy, or two adjacent substituents of Z join to form a benzene ring.

14. The compound of claim 13, wherein T is oxygen.

15. The compound of claim 13, wherein K is nitrogen; L is nitrogen; M is CH; T is oxygen; and Z is an unsubstituted phenyl group; a 3-fluoro phenyl group; a 2-methoxy phenyl group; a 4-nitro phenyl group; a 3-bromo phenyl group; a 2-phenoxy phenyl group; a 4-ethoxy phenyl group; a 2,4-dichloro phenyl group; a 2-chloro-3-methoxy phenyl group; a 3chloro-5-methoxy phenyl group; a 2-(E)-(CH$_3$O$_2$C—C=CH—OCH$_3$) phenyl group; a 3-cyano-4,6-difluoro phenyl group; a 2,6-difluoro phenyl group; a 2-nitro phenyl group; a 2-chloro-6CF$_3$ phenyl group; a 2-CF$_3$ phenyl group; a 2-fluoro-6-chloro phenyl group; a 4-fluoro phenyl group; a 2-cyano phenyl group; a 1-naphlhyl group; or a $C_6F_5$ group.

16. The compound of claim 13, wherein K is nitrogen; M is nitrogen; L is CH; T is oxygen; and Z is an unsubstituted phenyl group; a 3-fluoro phenyl group; a 2-methoxy phenyl group; a 4-nitro phenyl group; a 3-bromo phenyl group; a 2-phenoxy phenyl group; a 4-ethoxy phenyl group; a 2,4-dichloro phenyl group; a 2-chloro-3-methoxy phenyl group; a 3-chloro-5-methoxy phenyl group; a 2-(E)-(CH$_3$O$_2$C—C=CH—OCH$_3$) phenyl group; a 3-cyano-4,6-difluoro phenyl group; a 2,6-difluoro phenyl group; a 2-nitro phenyl group; a 2-chloro-6-CF$_3$ phenyl group; a 2-CF$_3$ phenyl group; a 2-fluorohloro phenyl group; a 4-fluoro phenyl group; a 2-cyano phenyl group; a 1-naphthyl group; or a $C_6F_5$ group.

17. The compound of claim 13, wherein K is CH: M is nitrogen; L is nitrogen; T is oxygen; and Z is an unsubstituted phenyl group; a 3-fluoro phenyl group; a 2-methoxy phenyl group; a 4-nitro phenyl group; a 3-bromo phenyl group; a 2-phenoxy phenyl group; a 4-ethoxy phenyl group; a 2,4-dichloro phenyl group; a 2-chloro-3-methoxy phenyl group; a 3-chloro-5-methoxy phenyl group; a 2-(E)-(CH$_3$O$_2$C—C=CH—OCH$_3$) phenyl group; a 3-cyano4,6-difluoro phenyl group; a 2,6-difluoro phenyl group; a 2-nitro phenyl group; a 2-chloro-6-CF$_3$ phenyl group; a 2-CF$_3$ phenyl group; a 2-fluoro-6-chloro phenyl group; a 4-fluoro phenyl group; a 2-cyano phenyl group; a 1-naphthyl group; or a $C_6F_5$ group.

18. The compound of claim 13, wherein K is nitrogen; L is nitrogen; M is CH; T is sulfur; and Z is an unsubstituted phenyl group; a 3-fluoro phenyl group; a 2-methoxy phenyl group; a 4-nitro phenyl group; a 3-bromo phenyl group; a 2-phenoxy phenyl group; a 4-ethoxy phenyl group; a 2,4-dichloro phenyl group; a 2-chloro-3-methoxy phenyl group; a 3-chloro-5-methoxy phenyl group; a 2-(E)CH$_3$O$_2$C—C=CH—OCH$_3$) phenyl group; a 3-cyano-4,6-difluoro phenyl group; a 2,6-difluoro phenyl group; a 2-nitro phenyl group; a 2-chloro-6CF$_3$ phenyl group; a 2-CF$_3$ phenyl group; a 2-fluoro-6-chloro phenyl group; a 4-fluoro phenyl group; a 2-cyano phenyl group; a 1-naphthyl group; or a $C_6F_5$ group.

19. The compound of claim 13, wherein K is nitrogen; L is CH; M is nitrogen; T is sulfur; and Z is an unsubstituted phenyl group; a 3-fluoro phenyl group; a 2-methoxy phenyl group; a 4-nitro phenyl group; a 3-bromo phenyl group; a 2-phenoxy phenyl group; a 4-ethoxy phenyl group; a 2,4-dichloro phenyl group; a 2-chloro-3-methoxy phenyl group; a 3chloro-5-methoxy phenyl group; a 2-(E)-(CH$_3$O$_2$C—C=CH—OCH$_3$) phenyl group; a 3-cyano-4,6-difluoro phenyl group; a 2,6-difluoro phenyl group; a 2-nitro phenyl group; a 2-chloro-6-CF$_3$ phenyl group; a 2-CF$_3$ phenyl group; a 2-fluoro-6-chloro phenyl group; a 4-fluoro phenyl group; a 2-cyano phenyl group; a 1-naphthyl group; or a $C_6F_5$ group.

20. The compound of claim 13, wherein K is CH; L is nitrogen; M is nitrogen; T is sulfur, and Z is an unsubstituted phenyl group; a 3-fluoro phenyl group; a 2-methoxy phenyl group; a 4-nitro phenyl group; a 3-bromo phenyl group; a 2-phenoxy phenyl group; a 4-ethoxy phenyl group; a 2,4-dichloro phenyl group; a 2-chloro-3-methoxy phenyl group; a 3-chloro-5-methoxy phenyl group; a 2-(E)-(CH$_3$O$_2$C—C=CH—OCH$_3$)phenyl group; a 3-cyano-4,6-difluoro phenyl group; a 2,6-difluoro phenyl group; a 2-nitro phenyl group; a 2-chloro-6-CF$_3$ phenyl group; a 2-CF$_3$ phenyl group; a 2-fluoro-6-chloro phenyl group; a 4-fluoro phenyl group; a 2-cyano phenyl group; a 1-naphthyl group; or a $C_6F_5$ group.

21. A fungicidal composition comprising a fungicidally effective amount of the compound of claim 13 and a fungicidally acceptable carrier or diluent thereof.

22. A method of combating fungi comprising applying to a plant, to a seed of a plant or to a locus of a plant or a seed a fungicidally effective amount of the compound of claim 13.

23. A compound of formula (IA) or a stereoisomer thereof:

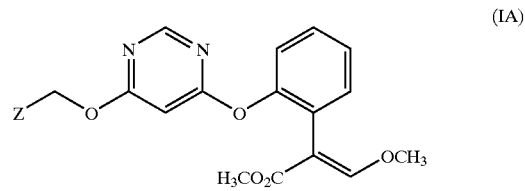

(IA)

wherein Z is an optionally substituted phenyl group; wherein the substituents are selected from one or more of the following: halo, hydroxy, oxo, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, $C_{2-4}$ alkenylthio, hydroxy($C_{1-4}$)alkyl, $C_{1-4}$ alkoxy ($C_{1-4}$)alkyl, $C_{3-6}$ cycloalkyl, $C_{3-6}$ cycloalkyl($C_{1-4}$)alkyl, phenyl, phenoxy, ($C_{1-4}$)alkanoyloxy, cyano, isocyano, thiocyanato, isothiocyanato, nitro, —NR'F", —N$_3$, —NHCONR'R", —NR'COR", —CONR'R, CR'=NOR", CHR'CO$_2$R', CSNR'R', —CO$_2$R', —OSO$_2$R', —SO$_2$R', —SOR', SO$_2$OR', SO$_2$NR'R", —COR', —OCOR', —CR'=NR", N=CHNR'R", NHSO$_2$R' or N=CR'R" in which R' and R" are independently hydrogen, hydroxy, $C_{1-4}$, alkyl, $C_{1-4}$ alkoxy, $C_{1-4}$ alkylthio, $C_{3-6}$ cycloalkyl, $C_{3-6}$ cycloalkyl($C_{1-4}$)alkyl, $C_{2-4}$ alkenyl, $C_{24}$ alkenyloxy, phenyl, phenoxy or benzyl, wherein the phenyl, phenoxy and benzyl groups are optionally substituted with halogen, $C_{1-4}$ alkyl or $C_{1-4}$ alkoxy, or two adjacent substituents of Z join to form a benzene ring.

24. The compound of claim 23, wherein Z is an unsubstituted phenyl group; a 3-fluoro phenyl group; a 2-methoxy phenyl group; a 4-nitro phenyl group; a 3-bromo phenyl group; a 2-phenoxy phenyl group; a 4-ethoxy phenyl group; a 2,4-dichloro phenyl group; a 2-chloro-3-methoxy phenyl group; a 3-chloro-5-methoxy phenyl group; a 2-(E)-(CH$_3$O$_2$C—C=CH—OCH$_3$) phenyl group; a 3-cyano-4,6-difluoro phenyl group; a 2,6-difluoro phenyl group; a 2-nitro phenyl group; a 2-chloro-6-CF$_3$ phenyl group; a 2-CF$_3$ phenyl group; a 2-fluoro-6chloro phenyl group; a 4-fluoro phenyl group; a 2-cyano phenyl group; a 1-naphthyl group; or a $C_6F_5$ group.

25. A fungicidal composition comprising a fungicidally effective amount of the compound of claim 23 and a fungicidally acceptable carrier or diluent thereof.

26. A method of combating fungi comprising applying to a plant, to a seed of a plant or to 6 a locus of a plant or a seed a fungicidally effective amount of the compound of claim 23.

* * * * *